(12) United States Patent
Hashi et al.

(10) Patent No.: US 8,057,535 B2
(45) Date of Patent: Nov. 15, 2011

(54) IMPLANTABLE MEDICAL DEVICE

(75) Inventors: Craig Hashi, Berkeley, CA (US); Daniel Francis Davidson, Alameda, CA (US)

(73) Assignee: Nano Vasc, Inc., Lafayette, CA (US)

( * ) Notice: Subject to any disclaimer, the term of this patent is extended or adjusted under 35 U.S.C. 154(b) by 0 days.

(21) Appl. No.: 13/069,116

(22) Filed: Mar. 22, 2011

(65) Prior Publication Data

US 2011/0166647 A1 Jul. 7, 2011

Related U.S. Application Data

(63) Continuation of application No. 12/630,682, filed on Dec. 3, 2009, which is a continuation-in-part of application No. 12/137,504, filed on Jun. 11, 2008.

(60) Provisional application No. 60/943,305, filed on Jun. 11, 2007.

(51) Int. Cl.
| | |
|---|---|
| A61F 2/06 | (2006.01) |
| A61F 2/00 | (2006.01) |
| A61L 33/00 | (2006.01) |
| A61K 31/727 | (2006.01) |
| B29C 47/00 | (2006.01) |

(52) U.S. Cl. ............. 623/1.43; 623/1.15; 623/1.32; 623/1.42; 623/1.44; 623/1.46; 424/423; 427/2.24; 427/2.25; 514/56; 264/465

(58) Field of Classification Search .......... 623/1.1, 623/1.32–1.33
See application file for complete search history.

(56) References Cited

U.S. PATENT DOCUMENTS

| | | |
|---|---|---|
| 3,357,432 A | 12/1967 | Sparks |
| 4,323,525 A | 4/1982 | Bornat |
| 4,552,707 A | 11/1985 | How |
| 5,084,065 A | 1/1992 | Weldon |
| 5,132,108 A | 7/1992 | Narayanan et al. |
| 5,134,192 A | 7/1992 | Feijen et al. |
| 5,549,663 A | 8/1996 | Cottone |
| 5,571,166 A | 11/1996 | Dinh |
| 5,575,815 A | 11/1996 | Slepian et al. |
| 5,607,475 A | 3/1997 | Cahalan et al. |

(Continued)

FOREIGN PATENT DOCUMENTS

EP 1258229 A1 11/2002

(Continued)

OTHER PUBLICATIONS

Hellener, et al. "Elastic Response of Filament Wound Arterial Prostheses Under Internal Pressure", Casali Institute of Applied Chemistry, Graduate School of Applied Sciences, The Hebrew University of Jerusalem, vol. 15, No. 14, Butterworth-Heinemann Ltd., 1994.

(Continued)

*Primary Examiner* — David Isabella
*Assistant Examiner* — Leslie Coburn
(74) *Attorney, Agent, or Firm* — Morgan, Lewis & Bockius LLP

(57) ABSTRACT

The invention provides an implantable medical device comprising a fibrous polymer body comprising a plurality of electrospun poly(urethane) fibers, a support filament wrapped around the body, an outer layer around the filament for adhering the filament to the body, the outer layer comprising a plurality of electrospun poly(urethane) fibers, and a polymer primer coating at least the fibers of the body. The polymer primer comprises poly(lactide) and is attached to a heparin residue through a link.

18 Claims, 14 Drawing Sheets

U.S. PATENT DOCUMENTS

| | | |
|---|---|---|
| 5,628,781 A | 5/1997 | Williams et al. |
| 5,628,788 A | 5/1997 | Pinchuk |
| 5,632,776 A | 5/1997 | Kurumatani et al. |
| 5,843,156 A | 12/1998 | Slepian et al. |
| 5,843,158 A | 12/1998 | Lenker |
| 5,866,217 A | 2/1999 | Stenoien et al. |
| 5,877,263 A | 3/1999 | Patnaik et al. |
| 5,916,585 A | 6/1999 | Cook et al. |
| 5,968,091 A | 10/1999 | Pinchuk et al. |
| 6,107,416 A | 8/2000 | Patnaik et al. |
| 6,120,847 A | 9/2000 | Yang et al. |
| 6,303,136 B1 | 10/2001 | Li et al. |
| 6,306,165 B1 | 10/2001 | Patnaik et al. |
| 6,338,904 B1 | 1/2002 | Patnaik et al. |
| 6,361,819 B1 | 3/2002 | Tedeschi et al. |
| 6,440,166 B1 | 8/2002 | Kolluri |
| 6,494,908 B1 | 12/2002 | Huxel |
| 6,604,925 B1 | 8/2003 | Dubson |
| 6,613,082 B2 | 9/2003 | Yang |
| 6,626,939 B1 | 9/2003 | Burnside |
| 6,627,422 B1 | 9/2003 | Li et al. |
| 6,702,848 B1 | 3/2004 | Zilla et al. |
| 6,713,568 B1 | 3/2004 | Patnaik et al. |
| 6,723,120 B2 | 4/2004 | Yan |
| 6,753,311 B2 | 6/2004 | Fertala et al. |
| 6,830,782 B2 | 12/2004 | Kanazawa |
| 6,833,004 B2 | 12/2004 | Ishii |
| 6,893,431 B2 | 5/2005 | Naimark et al. |
| 6,939,376 B2 | 9/2005 | Shulze |
| 7,029,495 B2 | 4/2006 | Stinson |
| 7,033,388 B2 | 4/2006 | Zilla |
| 7,037,527 B2 | 5/2006 | Bide et al. |
| 7,112,293 B2 | 9/2006 | Dubson et al. |
| 7,115,220 B2 | 10/2006 | Dubson et al. |
| 7,244,116 B2 | 7/2007 | Dubson et al. |
| 7,244,272 B2 | 7/2007 | Dubson et al. |
| 7,311,727 B2 | 12/2007 | Mazumder |
| 7,371,256 B2 | 5/2008 | Shalaby |
| 7,491,356 B2 | 2/2009 | Heikkila |
| 7,572,286 B1 | 8/2009 | Chen |
| 7,758,631 B2 | 7/2010 | Stinson |
| 7,824,601 B1 | 11/2010 | Stankus et al. |
| 2002/0049495 A1 | 4/2002 | Kutryk et al. |
| 2002/0084178 A1 | 7/2002 | Dubson |
| 2002/0090725 A1 | 7/2002 | Simpson et al. |
| 2002/0098278 A1 | 7/2002 | Bates et al. |
| 2002/0131933 A1 | 9/2002 | Delmotte |
| 2002/0161168 A1 | 10/2002 | Shalaby et al. |
| 2002/0169493 A1 | 11/2002 | Widenhouse et al. |
| 2002/0175449 A1 | 11/2002 | Chu et al. |
| 2003/0181856 A1 | 9/2003 | Goldman |
| 2003/0195611 A1 | 10/2003 | Greenhalgh et al. |
| 2004/0037813 A1 | 2/2004 | Simpson et al. |
| 2004/0052861 A1 | 3/2004 | Hatcher et al. |
| 2004/0063606 A1 | 4/2004 | Chu et al. |
| 2004/0146546 A1 | 7/2004 | Gravett |
| 2004/0204750 A1 | 10/2004 | Dinh |
| 2004/0214997 A1 | 10/2004 | Cima et al. |
| 2004/0241436 A1 | 12/2004 | Hsieh et al. |
| 2004/0259972 A1 | 12/2004 | Ringeisen et al. |
| 2004/0260318 A1 | 12/2004 | Hunter |
| 2004/0267362 A1 | 12/2004 | Hwang et al. |
| 2005/0003849 A1 | 2/2005 | Dubrow et al. |
| 2005/0175667 A1 | 8/2005 | Carlyle |
| 2005/0187605 A1 | 8/2005 | Greenhalgh et al. |
| 2005/0187607 A1 | 8/2005 | Akhtar |
| 2005/0214342 A1 | 9/2005 | Tweden et al. |
| 2005/0255230 A1 | 11/2005 | Clerc et al. |
| 2005/0276841 A1 | 12/2005 | Davis et al. |
| 2006/0009835 A1 | 1/2006 | Osborne |
| 2006/0064159 A1 | 3/2006 | Porter |
| 2006/0085063 A1 | 4/2006 | Shastri et al. |
| 2006/0129234 A1 | 6/2006 | Phaneuf et al. |
| 2006/0154063 A1 | 7/2006 | Fujihara et al. |
| 2006/0240110 A1 | 10/2006 | Kiick et al. |
| 2007/0043428 A1 | 2/2007 | Jennings |
| 2007/0050018 A1 | 3/2007 | Wainwright |
| 2007/0155273 A1 | 7/2007 | Chu et al. |
| 2007/0239267 A1 | 10/2007 | Hendriks |
| 2007/0244569 A1 | 10/2007 | Weber |
| 2007/0269481 A1 | 11/2007 | Li et al. |
| 2007/0276507 A1 | 11/2007 | Bertram |
| 2008/0154357 A1 | 6/2008 | Shalev |
| 2008/0195189 A1 | 8/2008 | Asgari |
| 2008/0195196 A1 | 8/2008 | Asgari |
| 2008/0199506 A1 | 8/2008 | Horres |
| 2008/0200975 A1 | 8/2008 | Dubson |
| 2008/0208316 A1 | 8/2008 | Shalev et al. |
| 2008/0208323 A1 | 8/2008 | El-Kurdi |
| 2008/0220042 A1 | 9/2008 | Hashi et al. |
| 2008/0306580 A1 | 12/2008 | Jenson |
| 2009/0018643 A1 | 1/2009 | Hashi et al. |
| 2009/0030504 A1 | 1/2009 | Weber et al. |
| 2009/0035350 A1 | 2/2009 | Stankus et al. |
| 2009/0043380 A1 | 2/2009 | Blaha et al. |
| 2009/0076588 A1 | 3/2009 | Weber |
| 2009/0118812 A1 | 5/2009 | Kokate et al. |
| 2009/0138070 A1 | 5/2009 | Holzer |
| 2009/0142505 A1 | 6/2009 | Orr |
| 2009/0143855 A1 | 6/2009 | Weber et al. |
| 2009/0187240 A1 | 7/2009 | Clerc |
| 2009/0227026 A1 | 9/2009 | Rapoport |
| 2009/0320435 A1 | 12/2009 | Bertsch et al. |
| 2010/0057197 A1 | 3/2010 | Weber et al. |
| 2010/0168837 A1 | 7/2010 | Magnuson et al. |
| 2010/0174351 A1 | 7/2010 | Ng et al. |
| 2010/0222873 A1 | 9/2010 | Atanasoska et al. |
| 2010/0239635 A1 | 9/2010 | Mclain et al. |

FOREIGN PATENT DOCUMENTS

| | | |
|---|---|---|
| WO | WO 98/53768 A | 12/1998 |
| WO | WO 2007094764 A2 | 8/2007 |
| WO | WO 2008041183 A2 | 4/2008 |
| WO | WO 2008070996 A1 | 6/2008 |
| WO | WO 2008112458 A2 | 9/2008 |
| WO | WO 2009042829 A1 | 4/2009 |
| WO | WO 2009101472 A2 | 8/2009 |
| WO | WO 2009101472 A3 | 8/2009 |

OTHER PUBLICATIONS

Drilling, et al.,"Fabrication of Burst Pressure Compotent Vascular Graft Via Electrospinning: Effects of Microstructure" J of Biomed Mater Res A., Mar. 15, 2009, vol. 88, No. 4; pp. 923-934.

Eberhart, et al, "A New Generation of Polyurethane Vascular Prostheses: Rara Avis or Ignis Fatuus?" Journal of Biomedical Material Research, 1999, vol. 48, No. 4; pp. 546-558.

Guarinoa, et al., "Polyactic Acid Fiber-reinforced Polycaprolactone Scaffolds for Bone Tissue Engineering" Biomaterials, Sep. 2008, vol. 29, Is. 27; pp. 3662-3670.

Hellener, et al., "Elastic Response of Filament Wound Arterial Prostheses under Internal Pressure", Biomaterials, 1994, vol. 15, No. 14; pp. 115-1121.

Kitazono, et al., "Tissue Engineering using Nanofiber", Journal of Synthetic Organic Chemistry Japan, May 2004, vol. 62, No. 5; pp. 514-519.

Kuraishi, et al. "Development of Nanofiber-covered Stents using Electrospinning: In Vitro and Acute Phase in Vivo Experiments" Journal of Biomedical Materials Research—Part B Applied Biomaterials, Jan. 2009, vol. 88, No. 1; pp. 230-239.

Loung-Van, et al, Controlled Release of Heparin from Poly(epsilon-caprolactone) Electrospun Fibers:, Biomaterials, Mar. 2005, vol. 27, No. 9; pp. 2042-2050.

Mann, B. et al., "Tethered-TGF-β increases extracellular matrix production of vascular smooth muscle cells", *Biomaterials* (2001) vol. 22, pp. 439-444.

Mario, et al., "Natural Origin Biodegradable System in Tissue Engineering and Regenerative Medicine; Present Status and Some Moving Trends", J.R. Soc. Interface, Dec. 22, 2007, vol. 4, No. 17; pp. 999-1030.

Matsuda, et al., "Mechno-active Scaffold Design of Small-Diameter Artificial Graft of Electrospun Segmented Polyurethane Fabrics", Apr. 1, 2005, vol. 73, No. 1; pp. 125-131.

Seidlits, et al., "Review Nanostructured Scaffolds for Neural Application" Nanomedicine, Apr. 2008, vol. 3, No. 2; pp. 183-199.

Stitzel, et al., Arterial Smooth Muscle Cell Proliferation on a Novel Biomimicking, Biodegradable Vascular Graft Scaffold:, Journal of Biomaterials Applications, Jul. 2001, vol. 16.

Wang, et al., "Fabrication and Properties of the Electrospun Polyactide/silk Fibroin-Gelatin Composite Tubular Scaffold", Biomacromolecules, Aug. 10, 2009, vol. 10, No. 8; pp. 2240-2244.

Xu, et al., "Electrospun Nanofiber Fabrication as Synthetic Extracellular Matrix and its Potential for Vascular Tissue Engineering" Tissue Engineering, Jul.-Aug. 2004, vol. 10, Nos. 7-8; pp. 1160-1168.

Yang, F. et al., "Electrospinning of nano/micro scale poly(L-lactic acid) aligned fibers and their potential in neural tissue engineering", *Biomaterials* (2005) vol. 26, No. 15, pp. 2603-2610.

Zuwei, M. et al., "Grafting of gelatin on electrospun poly(caprolactone) nanofibers to improve endothelial cell spreading and proliferation and to control cell orientation", *Tissue Engineering* (Jul.-Aug. 2005), vol. 11, No. 7-8, pp. 1149-1158.

32

IMPLANTABLE MEDICAL DEVICE

CROSS-REFERENCE TO RELATED APPLICATIONS

The present application is a Continuation of U.S. Non-Provisional application Ser. No. 12/630,682, filed on Dec. 3, 2009, currently pending, which is a Continuation-in-Part of U.S. Non-Provisional application Ser. No. 12/137,504, filed on Jun. 11, 2008, currently pending, which claims priority to U.S. Provisional Application 60/943,305, filed on Jun. 11, 2007, the entire disclosures of which are incorporated herein by reference in their entirety for all purposes.

BACKGROUND OF THE INVENTION

Treatment of various medical conditions commonly involves implantation of medical devices and prostheses into a body. Examples of implantable devices for treatment include a stent device or graft placed into a diseased vein or artery, a catheter, and a fistula. Other devices are partially or temporarily placed in a body or positioned external to a body. Implantable medical devices are commonly used in various medical applications including cardiovascular, urological, gastrointestinal, and gynecological applications.

Various implantable medical devices can be deployed within the lumen of a body vessel using minimally-invasive transcatheter techniques. For example, implantable medical devices can function as a stent, a shunt, or a replacement valve. Such devices can include an expandable frame configured for implantation in the lumen of a body vessel, such as an artery or a vein. Minimally-invasive techniques and instruments for placement of endoluminal and intralumenal medical devices have been developed to treat and repair undesirable conditions by implantation of a medical device at a body vessel.

The use of stent-graft medical devices, or other types of endoluminal mechanical support devices has developed into a primary therapy for lumen stenosis or obstruction. Stents in body lumens are commonly used to maintain open passageways such as the prostatic urethra, the esophagus, the biliary tract, intestines, and various coronary arteries and veins, as well as more remote cardiovascular vessels such as the femoral artery, etc. Stents and grafts may be designed for either temporary placement—to maintain the patency of the body lumen—or permanent placement. Grafts and similar devices are also commonly configured as artificial conduits.

A common problem with implantable vascular prostheses is intimal hyperplasia after intervention in the vessel, such as a coronary artery. For example, a significant percentage of arterial bypass grafts and vein grafts fail due to intimal hyperplasia after coronary bypass surgery. Endothelial denudation, platelet adherence, and leukocyte infiltration are some of the functions which can contribute to the proliferation of vascular smooth muscle cells (VSMCs) in the vessel and subsequent onset of arterial stenosis.

There is a need for an effective, biocompatible approach for securing an implantable medical device into or onto biological tissue within a body vessel. Existing approaches to securing implantable medical devices have had limited success. In one approach, the medical device is anchored to the surrounding tissues by physical or mechanical means. Another approach is directed to modifying the medical device surface or material to induce the production of fibrous (scar) tissue to anchor the medical device upon implantation within the body vessel.

There is a need to reduce or prevent the formation of biofilm and infection from bacteria and other microorganisms on catheters, orthopedic implants, pacemakers, contact lenses, stents, vascular grafts, embolic devices, aneurysm repair devices and other medical devices. There is also a need in the art for materials and structures that can replace or improve biological functions or promote the growth of new tissue in a subject. Tissue regeneration may be influenced by porosity among other factors.

Conventional grafts are made from various biocompatible plastics and metals such as poly(ethylene terephthalate) (PET). Such stents are known to cause irritation and undesirable biologic responses from the surrounding tissues in a lumen. Although conventional permanent medical devices are designed to be implanted for an extended period of time, it is sometimes necessary to remove the device prematurely, for example, because of poor patency or harsh biological responses. In this case, the device generally must be removed through a secondary surgical procedure. The surgical removal of the device will resultingly cause undesirable pain and discomfort to the patient and possibly additional trauma to the lumen tissue. In addition to the pain and discomfort, the patient must be subjected to an additional time consuming and complicated surgical procedure with the attendant risks of surgery.

Polyurethane (PU) and PU-based devices have commonly used for vascular grafts, blood conduits, and other devices for several decades. More recently, the use of PU for medical devices has been called into question. For example, PU-based vascular grafts have excellent records in animal trials but disappointing results in clinical applications. PU-based grafts have problematic long-term in vivo biostability and raise carcinogenic concerns as they degrade in the body. Thus, there is a need for implantable medical devices with biocompatibility, which is influenced by surface chemistry and topography.

Bioabsorbable and biodegradable materials have emerged more recently as a common material for medical devices. The conventional bioabsorbable or bioresorbable materials from which such stents and grafts are made are selected to absorb or degrade over time, thereby eliminating the need for subsequent surgical procedures to remove the stent from the body lumen. Such bioabsorbable and biodegradable materials also tend to have superior biocompatibility characteristics to biocompatible metals and other materials.

There are, however, known disadvantages associated with the use of bioabsorbable or biodegradable materials. One of the problems is that the materials break down at a faster rate than is desirable for the application. Premature degradation can lessen the affectivity of the device. Another problem is that conventional materials may break down into large, rigid fragments which may cause obstructions in the interior of a lumen, such as the urethra. Alternatively, the materials may take too long to breakdown and stay in the target lumen for a considerable period of time after their therapeutic use has been accomplished.

There is also the need to provide medical devices having mechanical compatibility or enhanced mechanical properties. For example, a mismatch between the stiffness, hardness, and porosity of the device in comparison to the surround tissue environment can cause irritation and other complications after implantation. In more drastic cases, the device can damage the tissue wall. There is also a need for devices have enhanced mechanical properties such as increased wall strength. Such properties may be useful for enabling easier navigation through the body and increased patency.

There is a need for medical devices and prostheses, and in particular implantable medical devices, which overcome these and other problems.

The information disclosed in this Background of the Invention section is only for enhancement of understanding of the general background of the invention and should not be taken as an acknowledgement or any form of suggestion that this information forms the prior art already known to a person skilled in the art.

SUMMARY OF THE INVENTION

Various aspects of the invention are directed to an implantable medical device comprising a fibrous polymer body comprising an electrospun poly(urethane) fiber, a support filament wrapped around the body, an outer layer around the filament for adhering the filament to the body, the outer layer comprising an electrospun poly(urethane) fibers; and a covering composition covering the fiber of the body. The covering composition comprises poly(lactide) and has the formula:

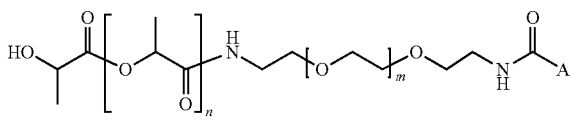

wherein A is a heparin residue, n is an integer between about 1000 and about 10000, and m is an integer between about 50 and about 100. In various embodiments, the body comprises a plurality of thermoplastic urethane fibers. In various embodiments, the filament comprises thermoplastic polyether urethane. In various embodiments, A is heparin sodium.

In various embodiments, the filament is configured to provide a degree of anti-kinking resistance to the device. The filament may be configured to prevent kinking of the device when bending at a radius greater than about 1 mm. The filament may be spirally wound around the body and has a pitch of between about 1 mm and about 6 mm. The filament may be spirally wound around the body and has a pitch of about 4 mm.

In various embodiments, the outer layer comprises a plurality of thermoplastic urethane fibers. In various embodiments, the body and outer layer each comprise a plurality of electrospun fibers and essentially all of the fibers of the body and outer layer is coated with the polymer primer. The body may be monolithically formed and the polymer primer may be integrated into the body by dip coating. In various embodiments, the body comprises a plurality of electrospun fibers, and the covering composition essentially fills interstices between the plurality of fibers. The polymer primer may be attached to the body by adsorption. In various embodiments, the device is a tubular vascular graft.

Various aspects of the invention are directed to a process for producing an implantable medical device comprising electrospinning a fibrous polymer body, the body comprising a plurality of electrospun fibers; wrapping a support filament around the electrospun body; providing an electrospun outer layer around the filament to adhere the filament to the body thereby forming an uncoated device; applying a polymer primer in a solution to the uncoated device under sufficient conditions to cause attachment of the primer to at least one of the plurality of fibers of the body; after the applying, immobilizing a linker molecule to the applied polymer primer, the linker molecule forming a covalent bond with the primer; and after the immobilizing, covalently attaching heparin residue to the immobilized linker molecule.

In various embodiments, the polymer primer solution has an inherent viscosity midpoint of about 2.0 dl/g at room temperature. In various embodiments, the applying is performed under sufficient conditions such that essentially all of the plurality of fibers of the body are covered with polymer primer. In various embodiments, the applying, immobilizing and attaching are accomplished by successive dip coating.

The devices and methods of the present invention have other features and advantages which will be apparent from or are set forth in more detail in the accompanying drawings, which are incorporated herein, and the following Detailed Description of the Invention, which together serve to explain certain principles of the present invention.

DETAILED DESCRIPTION OF THE PREFERRED EMBODIMENTS

Definitions and Abbreviations

Figure 1A:
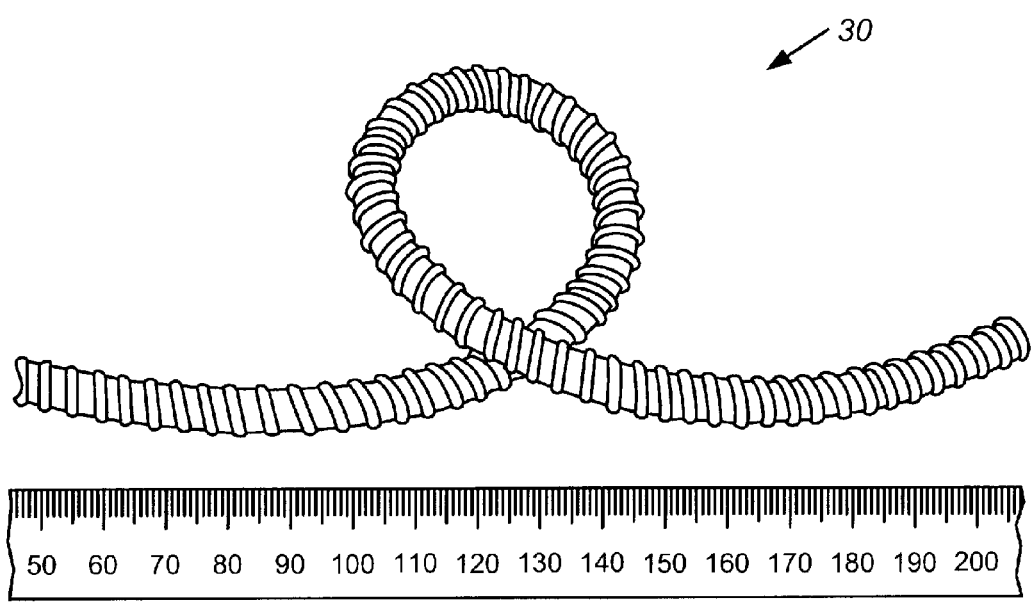
FIG. 1A is a perspective view of an exemplary implantable medical device in accordance with the present invention.
Figure 1B:
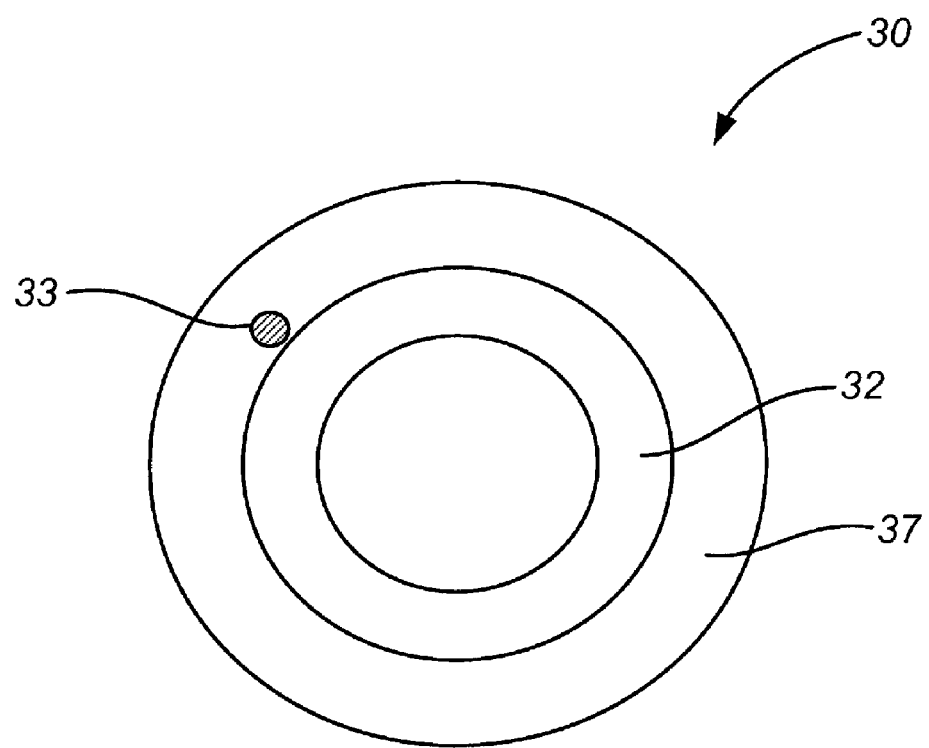
FIG. 1B is a cross-sectional, schematic view of the device of FIG. 1A, illustrating the various layers of the device.

The abbreviations and terminology used herein generally have their conventional meaning within the chemical, biological, and mechanical arts unless otherwise noted.

As used herein, the singular forms "a", "and", and "the" include plural referents unless the context clearly dictates otherwise.

"Fibrous" refers to structures formed of one or more fibers. The term "fiber" includes the singular and plural referents unless the context clearly dictates otherwise. In an exemplary embodiment, the device includes a body and outer layer formed of one or more fibers.

Stent, graft, stent-graft, venae cavae filter, endoprosthesis, and other implantable medical devices, collectively referred to hereinafter as a device, are typically, though not always, an intraluminal (e.g., intravascular) device capable of being implanted transluminally. In the case of a stent, the device may be self-expanding, expanded by an internal radial force, such as when mounted on a balloon, or a combination of self-expanding and balloon-expandable (hybrid expandable). The device may be implanted in a variety of body lumens or vessels such as within the vascular system, urinary tracts, bile ducts, fallopian tubes, coronary vessels, secondary vessels, etc. The device may be used to reinforce body vessels and to prevent restenosis following angioplasty in the vascular system.

As used herein, and unless otherwise indicated, a composition that is "essentially free" of a component means that the composition contains less than about 20% by weight, such as less than about 10% by weight, less than about 5% by weight, or less than about 3% by weight of the respective component.

"Peptide" refers to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, bioactive agents and the like may also be used in the invention. All of the amino acids used in the present invention may be either the D- or L-isomer. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, the term "copolymer" describes a polymer which contains more than one type of subunit. The term encompasses polymer which include two, three, four, five, six, or more types of subunits.

The term "isolated" refers to a material that is substantially or essentially free from components, which are used to produce the material. The lower end of the range of purity for the compositions is about 60%, about 70% or about 80% and the upper end of the range of purity is about 70%, about 80%, about 90% or more than about 90%.

The term "attached," as used herein encompasses interaction including, but not limited to, covalent bonding, ionic bonding, chemisorption, physisorption and combinations thereof.

The term "bioactive agent" as used herein refers to an organic molecule that has activity to produce a desired effect in a biological system. The organic molecule can be of biological origin, made by living organisms, or made synthetically. This includes, but is not limited to, antithrombogenic agents such as heparin.

"Small molecule," refers to species that are less than 1 kD in molecular weight, preferably, less than 600 D.

Where substituent groups are specified by their conventional chemical formulae, written from left to right, they equally encompass the chemically identical substituents, which would result from writing the structure from right to left, e.g., —$CH_2O$— is intended to preferably also recite —$OCH_2$—.

By "effective" amount of a drug, formulation, or permeant is meant a sufficient amount of an active agent to provide the desired local or systemic effect. A "therapeutically effective" amount refers to the amount of drug needed to affect the desired therapeutic result.

The term, "aligned", as used herein, refers to the orientation of fibers in a fibrous structure wherein at least 50% of the fibers are oriented in a general direction and their orientation forms an average axis of alignment. The orientation of any given fiber can deviate from the average axis of alignment and the deviation can be expressed as the angle formed between the alignment axis and orientation of the fiber. A deviation angle of 0° exhibits perfect alignment and 90° (or −90°) exhibits orthogonal alignment of the fiber with respect to the average axis of alignment. In an exemplary embodiment, the standard deviation of the fibers from the average axis of alignment can be an angle selected from between 0° and 1°, between 0° and 3°, between 0° and 5°, between 0° and 10°, between 0° and 15°, between 0° and 20°, or between 0° and 30°.

The term "rod", as used herein, refers to a fibrous polymer structure which is essentially in the shape of a filled cylinder. Spaces and channels can be present between the individual fibers which compose the rod.

The term "conduit", as used herein, refers to an object that is essentially cylindrical in shape. The conduit has an inner wall and an outer wall, an interior diameter, an exterior diameter, and an interior space which is defined by the inner diameter of the conduit as well as its length. Spaces and channels can be present between the individual fibers which compose the conduit.

The term "filled conduit", as used herein, refers to a conduit in which a portion of the interior space is composed of filler material. This filler material can be a fibrous polymer. Spaces and channels can be present between the individual fibers which compose the filled conduit.

The term "seam" or "seamed", as used herein, refers to a junction formed by fitting, joining, or lapping together two sections. These two sections can be held together by mechanical means, such as sutures, or by chemical means, such as annealing or adhesives. For example, a seam is formed by joining one region of a sheet to another region.

The term "seamless", as used herein, refers to an absence of a seam.

The term "cell" can refer to either a singular ("cell") or plural ("cells") situation.

The symbol , whether utilized as a bond or displayed perpendicular to a bond, indicates the point at which the displayed moiety is attached to the remainder of the molecule, for example, a polymer.

The term "poly(urethane)" and "polyurethane" as used herein refers to modified or unmodified polyurethanes, any co-polymer thereof, and blends or mixtures comprising said modified or unmodified polyurethanes and/or any co-polymer thereof. This includes, for example, thermoplastic and thermoset polyurethane elastomers, poly(ester urethane), poly(ester urethane)urea, polyether urethane, poly(ether ester urethane)urea, silicone polyether urethane, polycarbonate urethane, silicone polycarbonate urethane, segmented polycaprolactone polyurethane, and segmented polyethylene oxide polyurethane.

The term "poly(lactide)" and "polylactide" as used herein refers to poly(lactide) and blends including, but not limited to, poly(L-lactide), poly(D-lactide), poly(DL-lactide), poly(lactic acid) and combinations thereof. In various embodiments, the term "poly(lactide)" and "polylactide" encompasses copolymers of L-lactide, D-lactide, and/or DL-lactide with other types of subunits including, for example, poly(L-lactide-co-glycolide), poly(DL-lactide-co-glycolide), poly(DL-lactide-co-caprolactone), poly(L-lactide-co-caprolactone-co-glycolide), and combinations thereof.

The Implantable Device

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Turning now to FIGS. 1A, 1B, 2A, 2B, and 3, the present invention relates to a medical device, generally designated 30, configured for implantation into a body. In various embodiments, the device is an implantable vascular prostheses or vascular graft for the treatment of vascular disease. In various embodiments, the device is a vascular graft. In various embodiments, the device is configured for revascularizing tissue. In various embodiments, the device is an arteriovenous graft (A-V graft). One will appreciate from the description herein that the device of the present invention may be a variety of medical devices configured for different applications.

Exemplary device 30 includes a hollow, tubular inner wall structure or body, generally designated 32. The exemplary body is formed of a fibrous material. In various embodiments, the body (and the device formed therefrom) is a cylindrically-shaped structure which functions to hold open and/or expand a segment of a blood vessel or other lumen such as a coronary artery. In various embodiments, the device is configured for carrying biological fluids. In various embodiments, the device is configured for implantation into a human body.

An exemplary device of the invention possesses a unique set of properties: it can travel through small and tortuous body lumens to the treatment site. As will be understood by one of skill in the art, device 30 may dimensioned and configured to exhibit a very high modulus of elasticity, a very low yield point, a high tensile strength, a variable work hardening rate, good fatigue resistance, and/or flexibility for navigating the tortuous vascular anatomy. In various embodiments, the device is made of a material having a high degree of radiopacity or good corrosion resistance and biocompatibility to vascular tissue, blood and other bodily fluids.

In various embodiments, device 30 is an implantable medical device formed from a combination of fibrous polymer body 32, a support structure 33, and a covering composition 35 covering at least a portion of the fibers of the body. In an exemplary embodiment, the covering composition includes a polymer primer 36 functionalized with a bioactive agent 41 through one or more linkers 43. The exemplary body is formed of a plurality of polymer fibers.

Fibrous Body

In various embodiments, body 32 is fibrous polymer body. "Fibrous" and "fibrous structure" refer to an element formed of one or more fibers. In various embodiments, the body is formed of electrospun poly(urethane) fiber. "Fiber" refers to one or more fibers. In various embodiments, the body is formed of polymer fibers in random alignment. In various embodiments, the body is formed from a continuous fiber. In various embodiments, the plurality of polymer fibers are aligned in the longitudinal direction or the circumferential direction. In various embodiments, the body is monolithically formed.

A variety of materials can be used to form the body including synthetic and/or natural sources. In an exemplary embodiment, the body is formed from electrospun poly(urethane) fibers.

Body 32 is defined by an inner wall structure. One will appreciate that the body may be formed of a single electrospun fiber, such as a continuous filament, or may be formed of a plurality of fibers. One will appreciate that the actual wall thickness of the body may not be uniform because of the inherent nature of the fibrous structure. The electrospinning system may be adjusted to increase or decrease the variation in the wall structure.

In various embodiments, the inner wall structure has an average thickness of approximately 0.9 mm. In various embodiments, the inner wall structure has an average thickness of approximately 0.7 mm. In various embodiments, the inner wall structure is homogenous and has substantially uniform porosity. In various embodiments, the inner wall structure is formed by two or more layers of materials, such two layers of electrospun polymer fibers.

In a first aspect, the invention provides a body which comprises at least one layer composed of plurality of polymer fibers. A fibrous polymer layer includes a fiber or fibers which can have a range of diameters. In an exemplary embodiment, the average diameter of the fibers in the fibrous polymer layer is in the nanodiameter range. In various embodiments, the diameter is from about 0.1 nanometers to about 50000 nanometers. In another exemplary embodiment, the average diameter of the fibers in the fibrous polymer layer is from about 25 nanometers to about 25,000 nanometers. In an exemplary embodiment, the average diameter of the fibers in the fibrous polymer layer is from about 50 nanometers to about 20,000 nanometers. In an exemplary embodiment, the average diameter of the fibers in the fibrous polymer layer is from about 100 nanometers to about 5,000 nanometers. In an exemplary embodiment, the average diameter of the fibers in the fibrous polymer layer is from about 1,000 nanometers to about 20,000 nanometers. In an exemplary embodiment, the average diameter of the fibers in the fibrous polymer layer is from about 10 nanometers to about 1,000 nanometers. In an exemplary embodiment, the average diameter of the fibers in the fibrous polymer layer is from about 2,000 nanometers to about 10,000 nanometers. In an exemplary embodiment, the average diameter of the fibers in the fibrous polymer layer is from about 0.5 nanometers to about 100 nanometers. In an exemplary embodiment, the average diameter of the fibers in the fibrous polymer layer is from about 0.5 nanometers to about 50 nanometers. In an exemplary embodiment, the average diameter of the fibers in the fibrous polymer layer is from about 1 nanometer to about 35 nanometers. In an exemplary embodiment, the average diameter of the fibers in the fibrous polymer layer is from about 2 nanometers to about 25 nanometers. In an exemplary embodiment, the average diameter of the fibers in the fibrous polymer layer is from about 90 nanometers to about 1,000 nanometers. In an exemplary embodiment, the average diameter of the fibers in the fibrous polymer layer is from about 500 nanometers to about 1,000 nanometers.

In an exemplary embodiment, the fibrous body is formed from one or more a nanofiber or microfiber polymer layers. Microfiber polymer layers have micron-scale features (an average fiber diameter between about 1,000 nanometers and about 50,000 nanometers, and in various embodiments between about 1,000 nanometers and about 20,000 nanometers), while nanofiber polymer layers generally have submicron-scale features (an average fiber diameter between about 10 nanometers and about 1,000 nanometers, and in various embodiments between about 50 nanometers and about 1,000 nanometers).

In an exemplary embodiment, the average diameter of the fibers in the fibrous polymer layer is in the microdiameter range. In an exemplary embodiment, the fibers have an average diameter in the range selected from between about 100 nanometers to about 8 micrometers, from about 500 nanometers to about 5 micrometers, and from about 1 micrometer to about 3 micrometers. One will appreciate that the dimensions and configuration of the fibers in the fibrous polymer elements of the device may vary depending on the application. Each of these polymer layers can resemble the physical structure at the area of treatment, such as native collagen fibrils or other extracellular matrices.

In some embodiments, the fibrous body is composed of a single continuous fiber. In other embodiments, the fibrous body is composed of at least two, three, four, five, or more fibers. In an exemplary embodiment, the number of fibers in the fibrous body is a member selected from 2 to 100,000. In an exemplary embodiment, the number of fibers in the fibrous body is a member selected from 2 to 50,000. In an exemplary embodiment, the number of fibers in the fibrous body is a member selected from 50,000 to 100,000. In an exemplary embodiment, the number of fibers in the fibrous body is an integer between about 10 and about 20,000. In an exemplary embodiment, the number of fibers in the fibrous body is an integer between about 15 and about 1,000.

The fibrous polymer body can comprise a fiber of at least one composition. In an exemplary embodiment, the fiber or fibers of the fibrous polymer body are biodegradable.

In an exemplary embodiment, the device includes biodegradable polymers. Biodegradable polymers are those which are approved by the FDA for clinical use. In another exemplary embodiment, biodegradable polymer layers are used to guide the morphogenesis of engineered tissue and gradually degrade after the assembly of the tissue. The degradation rate of the polymers can be tailored by one of skill in the art to match the tissue generation rate. Additional ways to increase polymer layer biodegradability can involve selecting a more hydrophilic copolymer (for example, polyethylene glycol), decreasing the molecular weight of the polymer, as higher molecular weight often means a slower degradation rate, and changing the porosity or fiber density, as higher porosity and lower fiber density often lead to more water absorption and faster degradation. In another exemplary embodiment, the tissue is vascular tissue.

Spiral Filament

Device 30 includes support structure 33 for providing a degree of anti-kinking and compression resistance. In various embodiments, the support structure is a filament spirally wound around at least a portion or the entire body 32. "Degree of anti-kinking resistance" refers to a structure that mechanically supports the device and/or measurably decreases the minimum bending radius at which kinking occurs.

Suitable materials for support structure 33 include, but are not limited to, thermoplastic polyether urethane. The exemplary filament support extends around the body in a spiral or corkscrew fashion. The filament may be wound manually and hand-tightened. The exemplary filament covers most, if not all, of the length of the inner wall structure.

The exemplary spiral filament has a diameter of 0.028 inches. In various embodiments, the filament windings have a sufficient pitch to resist kinking of the device resistance when bending at a radius greater than about 1 mm. In various embodiments, the pitch is between about 1 mm and about 6 mm. In various embodiments, the pitch is between about 2 mm and 4 mm. In various embodiments, the pitch is about 4 mm. One will appreciate from the description herein that the filament dimensions and configuration may be varied depending on the dimensions and application of the fibrous body and device formed therefrom.

Device 30 includes an outer or overwrap layer 37 which wraps around support structure 33 to adhere the support structure to the body. The outer layer wraps around and covers at least a portion of the support structure and/or body.

In various embodiments, the outer layer is formed of the same material as the body. In an exemplary embodiment, the outer layer is formed of electrospun poly(urethane) fiber. The fiber forming the outer layer may be one or more fiber elements. Similar to the body 32, outer layer 37 may be formed of a single electrospun fiber, such as a continuous filament, or may be formed of a plurality of fibers.

It will be appreciated that the outer layer of the present invention serves several purposes. The outer layer secures the filament to the device body. The outer layer also insulates the filament from the environment in which the device is placed. Thus, the rough surface of the filament on the body is less likely to cause complications after placement. The outer layer also serves to reduce the risk of problems related to damage and weakening of the device body and reduced tissue infiltration. In various embodiments, the outer layer encapsulates the filament in a sandwich configuration with the outer surface of the body thereby providing an increased level of integration into the resulting device.

Covering Composition and Bioactive Agent

Exemplary device 30 includes a covering composition 35 which covers at least one of the electrospun fibers of body 32. The exemplary covering composition includes polymer primer 36 which covers or coats the fibers and a bioactive agent 41 attached to the polymer primer through a linker molecule 43. Thus, the exemplary linker molecule and bioactive agent effectively coat the fibers via the polymer primer.

In various embodiments, the polymer primer coats all of the fibers of the body. In various embodiments, the polymer primer coats at least one of the fibers in outer layer 37. In various embodiments, each individual fiber is coated or encapsulated by the polymer primer. In various embodiments, the polymer primer coats support structure 33.

In various embodiments, the covering composition covers all of the fibers of the body. In various embodiments, the covering composition covers at least one of the fibers in outer layer 37. In various embodiments, each individual fiber is coated, encapsulated, or covered by the covering composition. In various embodiments, the covering composition covers support structure 33.

Suitable materials for the polymer primer include, but are not limited to, bioabsorbable polymers. In various embodiments, the polymer primer is formed of a poly(lactide). In various embodiments, the polymer primer includes poly(D,L-lactide) ("PDLA"). In various embodiments, at least one of the polymer primer, body, and outer layer is biodegradable.

Exemplary bioactive agent 41, which is attached to polymer primer 36, serves to functionalize the coated fiber. In various embodiments, the bioactive agent and linker molecule are referred to as layers formed on top of the polymer primer layer.

In various embodiments, the bioactive agent is attached to the polymer primer through a linker molecule. As will be discussed below, the attachment may be accomplished by the use of linker molecules, catalysts, and/or coupling agents. In various embodiments, a heparin residue is attached to a PDLA polymer primer through at least one linker. In various embodiments, heparin is covalently attached to a PDLA polymer primer through a di-amino poly(ethylene glycol) ("PEG") linker.

In various embodiments, the covering composition includes a polymer primer functionalized with a bioactive agent. In various embodiments, the covering composition comprises poly(lactide) and has the formula:

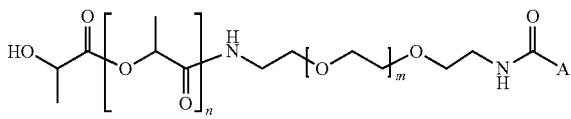

wherein A is a heparin residue, n is an integer between about 1000 and about 10000, and m is an integer between about 50 and about 100. One will appreciate that m and n can be chosen based on a variety of commercially available products. In various embodiments, m is an integer in a range selected from between about 1 and about 500, between about 50 to about 100, about 60 to about 85, and about 66 to about 83. In various embodiments, the average value of m is about 74. In various embodiments, n is an integer in a range selected from between about 1000 to about 700000, between about 3000 to about 10000, between about 4000 to about 8500, and between about 4100 and about 7300. In various embodiments, the average value of n is about 7250. In various embodiments, n is of a sufficient number to provide an average inherent viscosity midpoint in a range selected from between about 0.1 to about 6.0 dL/g, between about 1 to about 4 dL/g, and between about 1.6 to about 2.4 dL/g, at room temperature. In various embodiments, n is of a sufficient number to provide an average inherent viscosity midpoint of about 2.0 dL/g at room temperature.

In various embodiments, the polymer primer comprises PDLA and a linker molecule is immobilized to an end of the PDLA. In various embodiments, the linker molecule has a molecular weight in a range selected from the group consisting of between about 1000 g/mol and about 10000 g/mol, between about 2500 g/mol and about 4500 g/mol, between about 2800 g/mol and about 4000 g/mol, between about 3000 g/mol and about 3700 g/mol. In various embodiments, the linker is PEG and has a molecular weight of about 3350 g/mol. In various embodiments, the polymer primer has a molecular weight in a range selected from the group consisting of between about 1000 g/mol and about 800000 g/mol, between about 200000 g/mol and about 600000 g/mol, between about 250000 g/mol and about 550000 g/mol, between about 290000 g/mol and about 530000 g/mol. In various embodiments, the polymer primer has a molecular weight of about 406000 g/mol.

Exemplary bioactive agent 41 is attached to the polymer primer 36 through a linker. In various embodiments, the linker is a polymer or subunit which is a member selected from an aliphatic polyester, a polyalkylene oxide, and combinations thereof.

In an exemplary device, each fiber is coated with poly(lactide) (PLA) and functionalized with a heparin residue via a linker molecule. In various embodiments, the linker molecule is PEG. The PEG is immobilized to the surface of the poly(lactide) primer layer using carbodiimide chemistry (i.e., activation of free carboxylic acid residues of the PLA coating with a coupling agent and subsequent reaction with one of the functional ends of di-amino PEG). In various embodiments, the heparin residue is attached to the linker molecule using carbodiimide chemistry (i.e., activation of free carboxylic acid residues on the heparin and subsequent reaction with the remaining functional end of the immobilized linker molecule). In various embodiments, the linker molecule tethers the heparin from the surface of the respective polymer fiber.

In various embodiments, the linker molecule is PEG, and the PEG is immobilized to the surface of the poly(lactide) coating layer. The PEG is of linear structure and has an average molecular weight of 3350 g/mol. The average molecular weight of the PEG may be between about 1000 and 10,000 g/mol. In various embodiments, the heparin residue is attached to the linker molecule using carbodiimide chemistry. In various embodiments, the linker molecule tethers the heparin from the surface of the respective polymer fiber.

In an exemplary embodiment, poly(lactide) primer layer 36 is attached to the fibrous body by adsorption. In various embodiments, the poly(lactide) layer is integrated into the fibrous body. In various embodiments, the poly(lactide) layer forms a covalent bond with the linker molecule. In various embodiments, the linker molecule forms a covalent bond with the heparin residue. In various embodiments, the bioactive agent is covalently associated with the poly(lactide) polymer primer through at least one linker molecule.

In various embodiments, polymer primer 36 is an aliphatic polyester that is linear or branched. In an exemplary embodiment, the linear aliphatic polyester is a member selected from lactic acid (D- or L-), lactide, poly(lactic acid), poly(lactide) glycolic acid, poly(lactide-co-glycolide), poly(lactic acid-co-glycolic acid), and combinations thereof. In another exemplary embodiment, the aliphatic polyester is branched and comprises at least one member selected from lactic acid (D- or L-), poly(D,L-lactide), lactide, poly(lactic acid), poly(lactide), poly(lactide-co-glycolide), poly(lactic acid-co-glycolic acid), and combinations thereof which is conjugated to a linker or a bioactive agent. In an exemplary embodiment, the polyalkylene oxide is a member selected from polyethylene oxide, polyethylene glycol, polypropylene oxide, polypropylene glycol and combinations thereof.

In some embodiments, the bioactive agent is utilized to promote the growth of new tissue. In an exemplary embodiment, the bioactive agent is a member selected from heparin, heparin sulfate, heparin sulfate proteoglycan and combinations thereof. In various embodiments, "heparin residue" may refer to clinical analogs such as anti-platelet agents. Other agents that are useful in conjunction with the present invention will be readily apparent from the description herein to those of skill in the art. In various embodiments, the bioactive agent is a heparin residue such as heparin sodium. Heparin is a biological substance, sometimes made from pig intestines. It works by activating antithrombin III, which blocks thrombin from clotting blood. In an exemplary embodiment, the bioactive agent is heparin or a prodrug of heparin. In an exemplary embodiment, the device includes a heparin analog or a prodrug of a heparin analog. In an exemplary embodiment, the heparin analog is a member selected from Antithrombin III, Bemiparin, Dalteparin, Danaparoid, Enoxaparin, Fondaparinux (subcutaneous), Nadroparin, Parnaparin, Reviparin, Sulodexide, and Tinzaparin.

In various embodiments, the bioactive agent that is capable of retarding or arresting the formation of intimal hyperplasia is appropriate for incorporation into the fiber of the invention. Although the discussion thus far has focused on vascular reconstructive surgery involving implanting a vascular graft, those of skill will readily appreciate that the discussion is generally applicable to other forms of vascular reconstructive surgery, angioplasty and preventing the formation of post-surgical adhesions in other organs and/or internal structures.

Polymer primer 36 may coat each or most of the respective fibers of device 30 or may be incorporated or impregnated into the fibrous structure. For example, the polymer primer may fill interstices between the fibers. "Fill interstices" refers to the polymer primer existing in the space between adjacent fibers. In an exemplary embodiment, the polymer primer covers or coats essentially all of each of the fibers and thereby fills interstices between the fibers. "Cover" is to be understood as commonly used in the chemical and biological arts and refers to covering a portion or all of an element. In an exemplary embodiment, the polymer primer covers essentially all of the fibers of the body, and each fiber is substantially coated by the polymer primer. One will appreciate from the description herein that the covering composition is associated with the device by virtue of the polymer primer.

One or more of the many art-recognized techniques for immobilizing, coating, adhering, or attaching one molecule with another molecule or surface can be used to prepare the device. These methods include, but are not limited to, covalent attachment to the respective molecule or a derivative of the molecule bearing a "handle" allowing it to react with a component of the fiber having a complementary reactivity.

In various embodiments, the bioactive agent is covalently attached to a linker molecule which is covalently attached to the polymer primer. In various embodiments, the polymer primer is non-covalently associated with fibrous body 32. Non-covalent association can also be termed "embedded" or "impregnated" and includes, but is not limited to, chemisorption, physisorption and combinations thereof.

Methods of Making the Device

Figure 10:
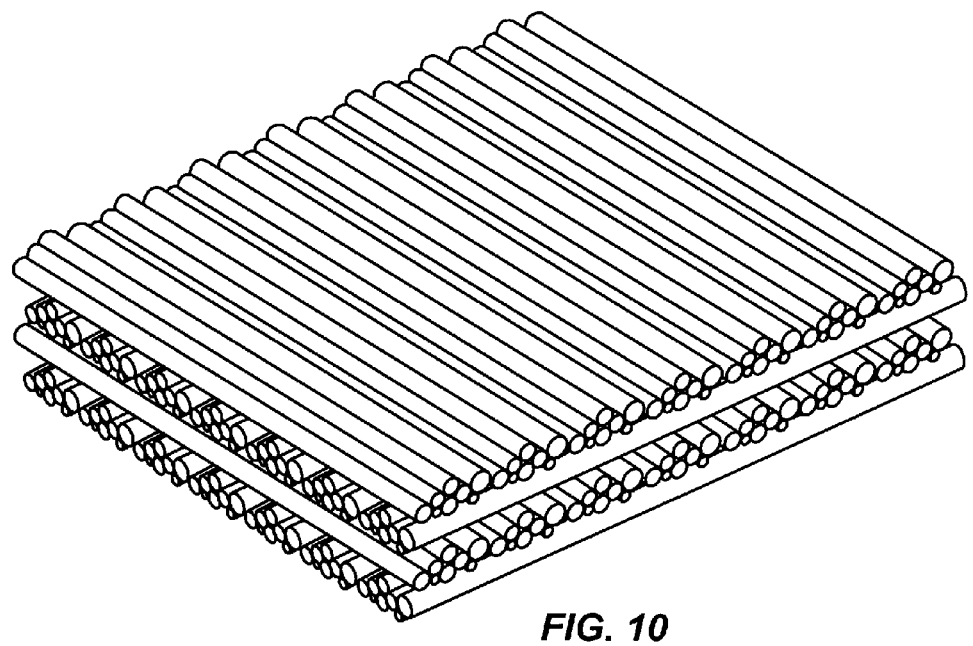
FIG. 10 is an illustration of a 'criss-cross' sheet similar to FIG. 8 which comprises aligned sheets.
Figure 11:
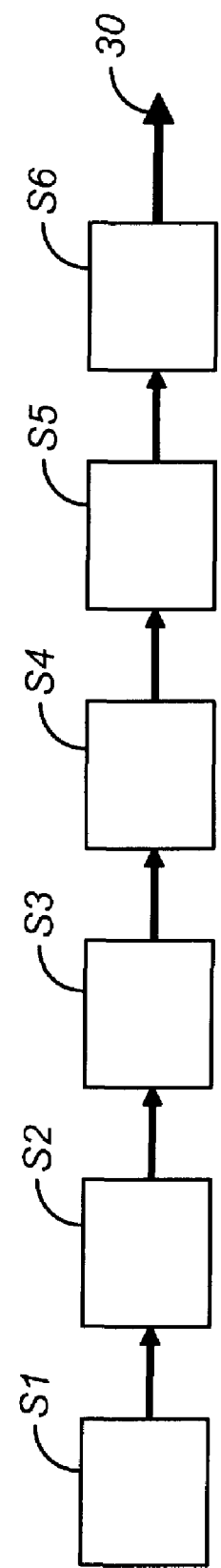
FIG. 11 is a flow diagram showing the process for making the device of FIG. 1A.

Turning to FIGS. 3-6, 7A, 7B, and 8-11, an exemplary method of making device 30 in accordance with the present invention will now be described. Fibrous polymer body 32 can be produced in a variety of ways. FIG. 11 provides a flowchart illustrating a general process for producing device 30 in accordance with the present invention.

Figure 4:
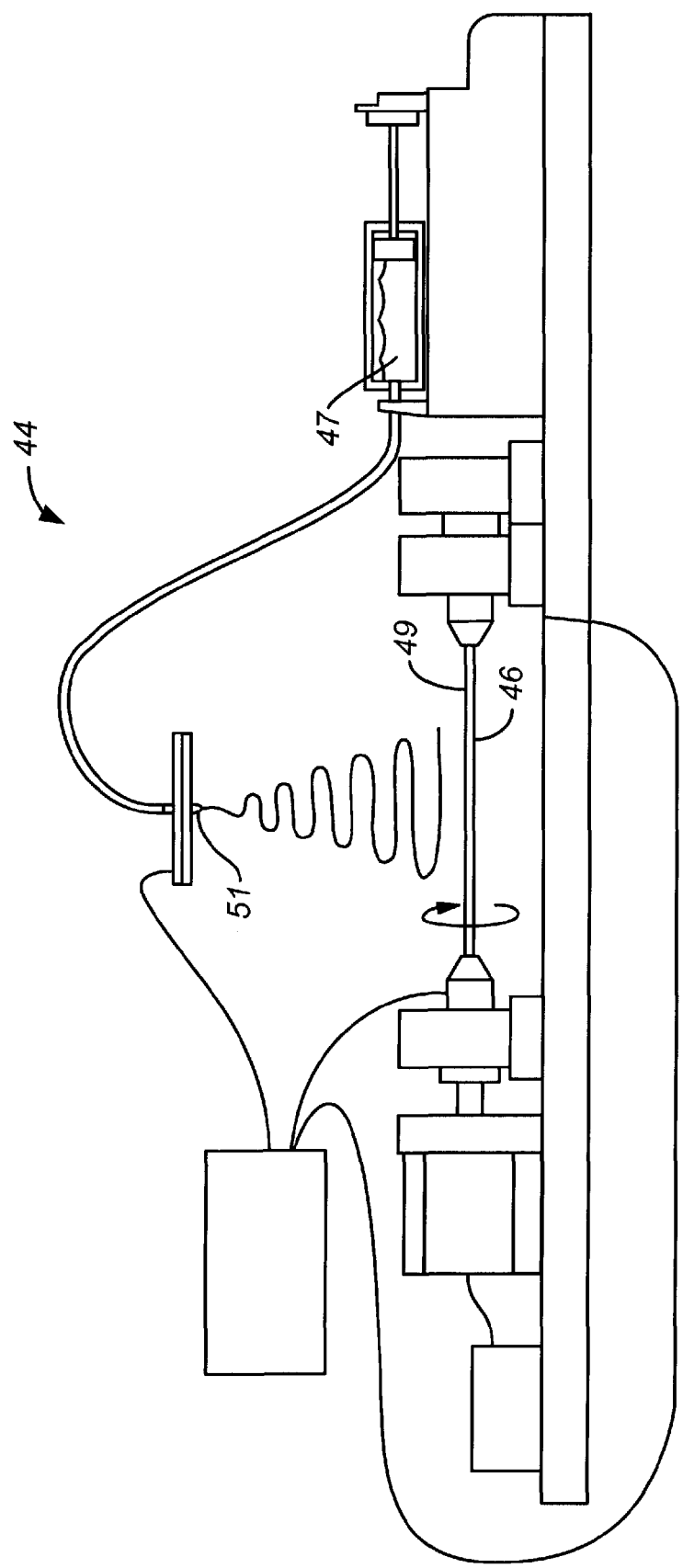
FIG. 4 is a schematic view of an electrospinning apparatus and mandrel for forming the device of FIG. 1A in accordance with the present invention.
Figure 5:
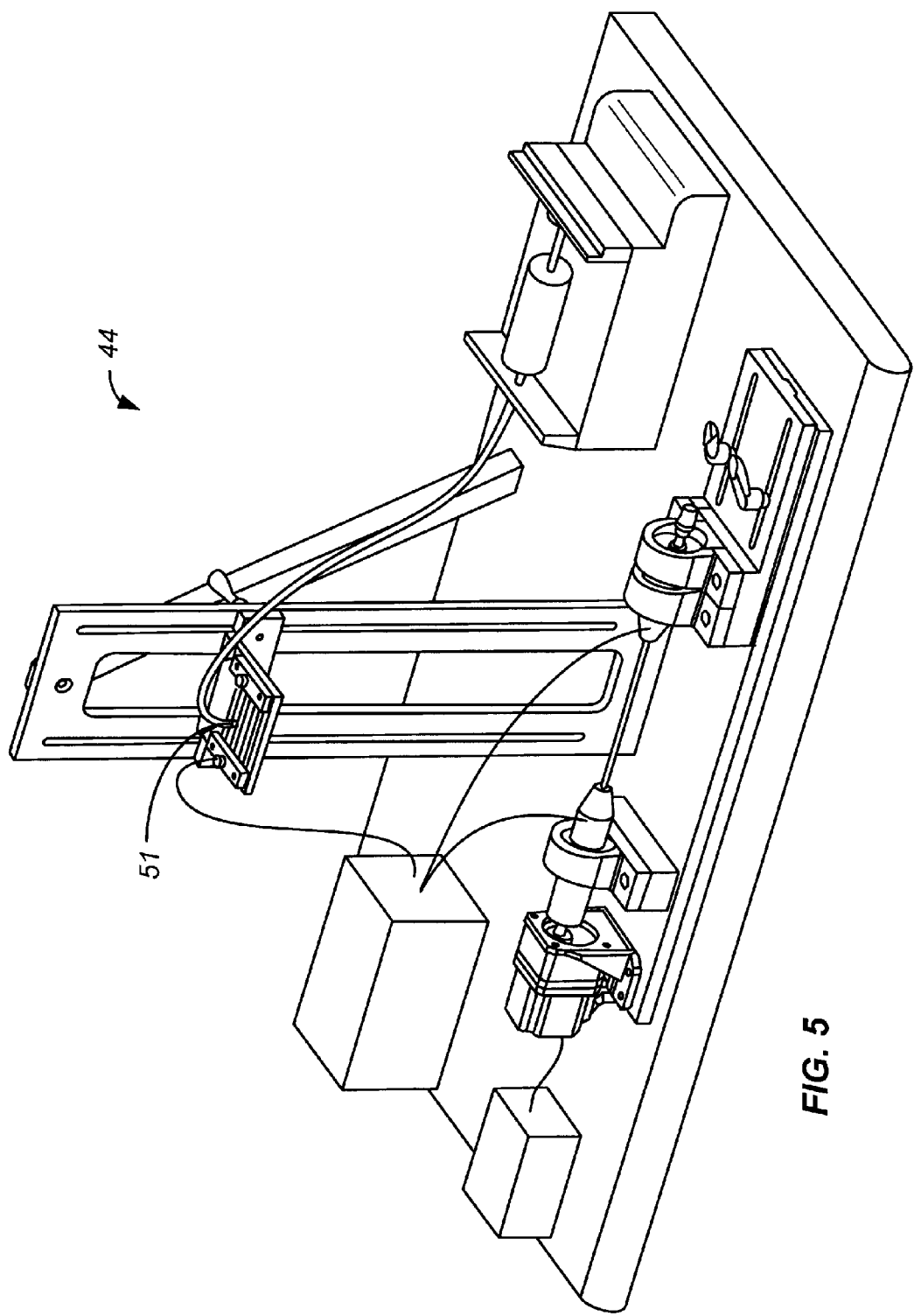
FIG. 5 is a perspective view of the electrospinning apparatus of FIG. 4.
Figure 6:
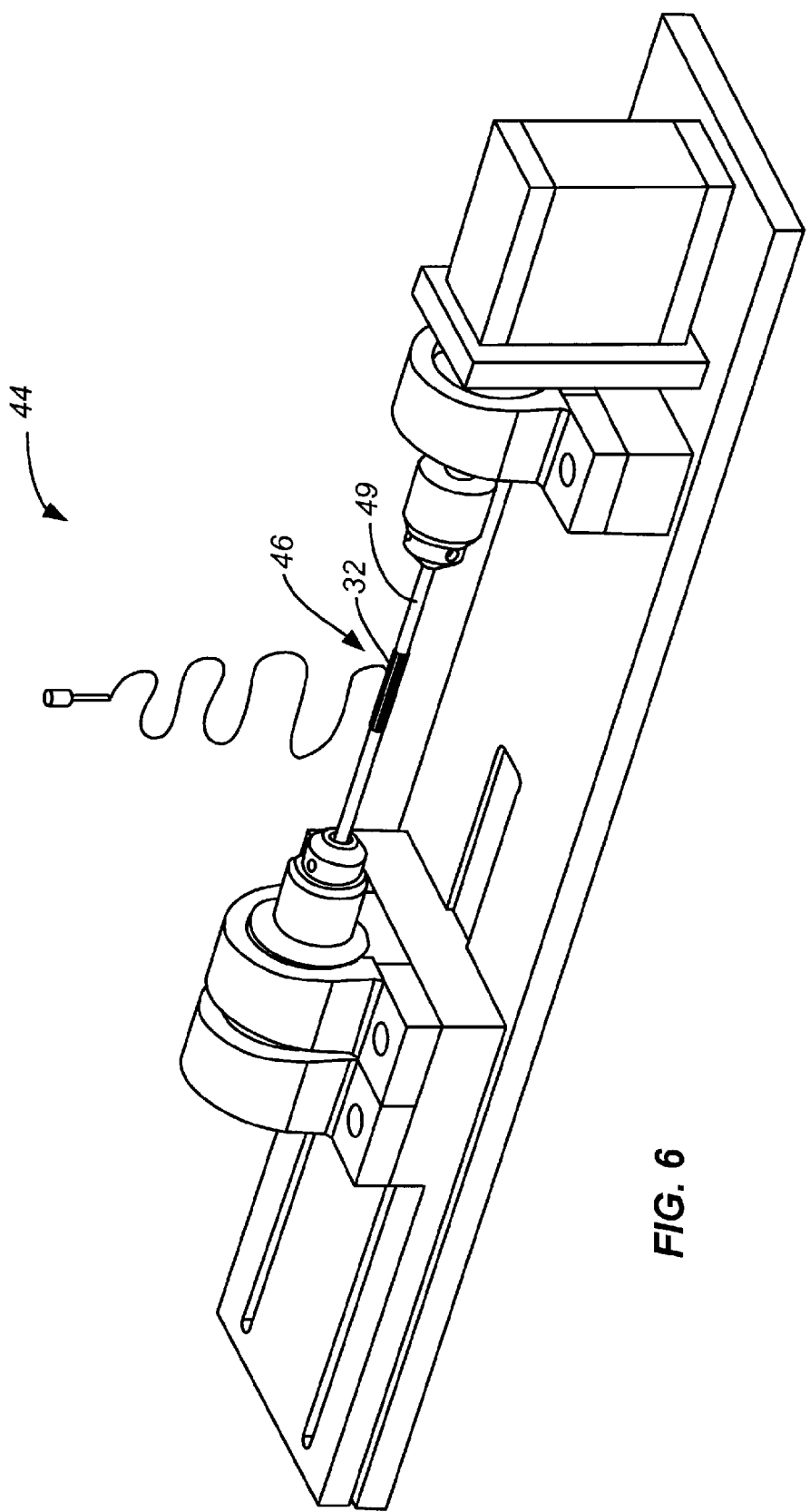
FIG. 6 is an enlarged view of a portion of the electrospinning apparatus of FIG. 5, illustrating forming of a polymer body.

In Step S1, fibrous body 32 is produced by electrospinning a plurality of polymer fibers into a first tubular layer on a mandrel (FIGS. 4, 5, and 6). The exemplary polymer fibers are poly(urethane) and have an average diameter between about 1 micrometer and about 3 micrometers.

Electrospinning is a process that exploits the interactions between an electrostatic field and a conducting fluid. The fluid is deployed to a substrate such as a rotating mandrel. One will appreciate that other methods may be used to produce the device including, but not limited to, other forms of electrostatic processing, deposition, and etching.

After electrospinning, extrusion and molding can be utilized to further fashion the polymers. To modulate fiber organization into aligned fibrous polymer layers, the use of patterned electrodes, wire drum collectors, or post-processing methods such as uniaxial stretching has been successful. Further details regarding the electrospinning process may be found in the above-mentioned U.S. application Ser. No. 12/137,504, which is incorporated herein for all purposes by this reference.

FIGS. 4, 5, and 6 illustrate an exemplary electrospinning system, generally designated 44, in accordance with the invention. The exemplary system includes a mandrel 49 having a contact region 46, spinneret 51 for dispensing a polymer fluid, and a reservoir 47 for holding the fluid.

The polymer solution forming the basis for the electrospun fibrous body can be produced in one of several ways. One method involves polymerizing the monomers and dissolving the subsequent polymer in appropriate solvents. This process can be accomplished in a syringe assembly or it can be subsequently loaded into a syringe assembly.

The polymer used to form the exemplary body is first dissolved in a solvent. The solvent can be any solvent which is capable of dissolving the polymer monomers and/or subunits and providing a polymer solution capable of conducting and being electrospun. Typical solvents include a solvent selected from N,N-Dimethyl formamide (DMF), tetrahydrofuran (THF), methylene chloride, dioxane, ethanol, hexafluoroisopropanol (HFIP), chloroform, water and combinations thereof. In an exemplary embodiment, the body is formed of a plurality of electrospun poly(urethane) fibers. In various embodiments, the fibers are formed by dissolving poly(urethane) in N,N-dimethylformamide (DMF) to approximately 22% weight/volume.

The poly(urethane) solution is spun on a mandrel 49. The mandrel is mechanically attached to a motor, often through a drill chuck. In an exemplary embodiment, the motor rotates the mandrel at a speed of between about 1 revolution per minute (rpm) to about 500 rpm. In an exemplary embodiment, the motor rotation speed is between about 200 rpm to about 500 rpm. In another exemplary embodiment, the motor rotation speed is between about 1 rpm to about 100 rpm. In various embodiments, mandrel is negatively charged and one or more spinnerets 51 for dispensing the polymer is positively charged.

In an exemplary embodiment, the electrospinning is conducted in a controlled environment. In various embodiments, the environment temperature is in a range selected from about 5 degrees Celsius to about 15 degrees Celsius, from about 15 degrees Celsius to about 30 degrees Celsius, from about 30 degrees Celsius to about 45 degrees, and more than 45 degrees Celsius. The temperature is optionally controlled using infrared (IR) heat. In various embodiments, the local, relative humidity of the environment is in a range selected from about 0% to about 5%, from about 5% to about 15%, from about 15% to about 20%, from about 20% to about 25%, from about 25% to about 30%, and about 30% to about 90%. The height of the spinnerets above the mandrel is fixed.

Figure 7A:
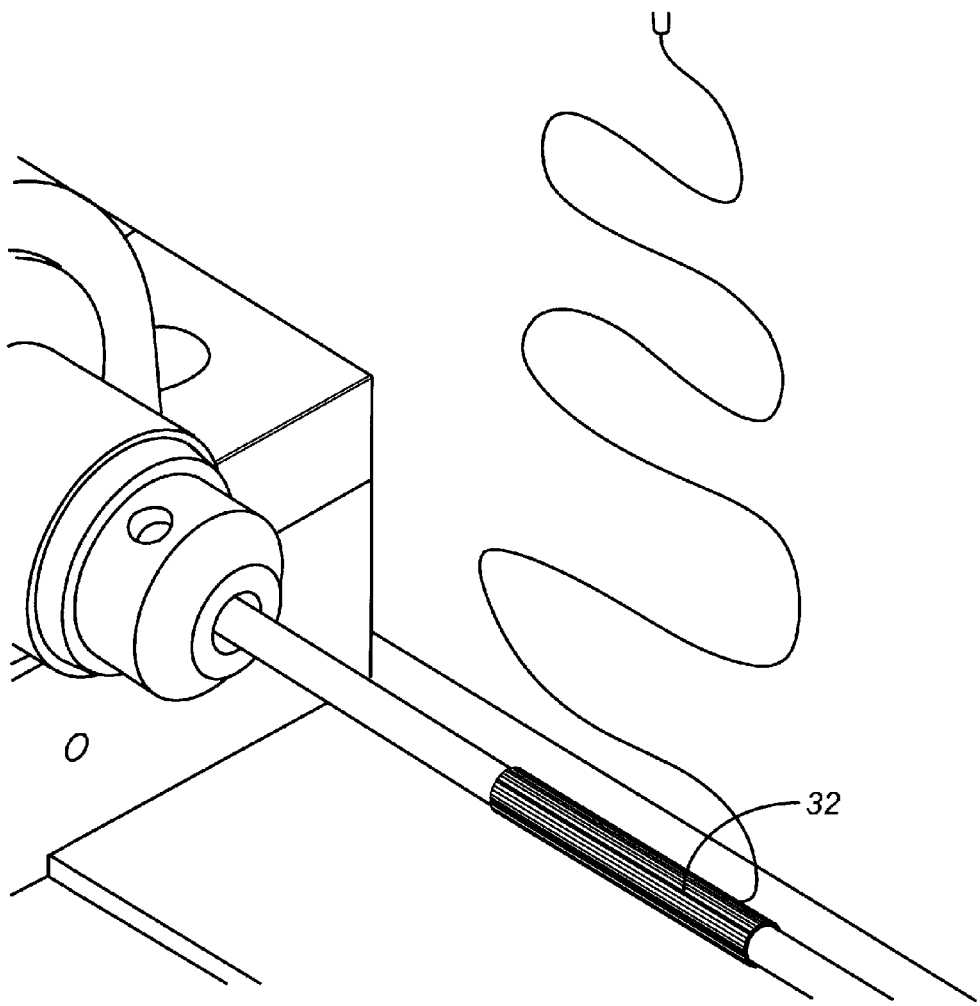
FIG. 7A is an enlarged view of a portion of the electrospinning apparatus of FIG. 5, illustrating the deposition of a longitudinally aligned fiber layer on a on the mandrel.
Figure 7B:
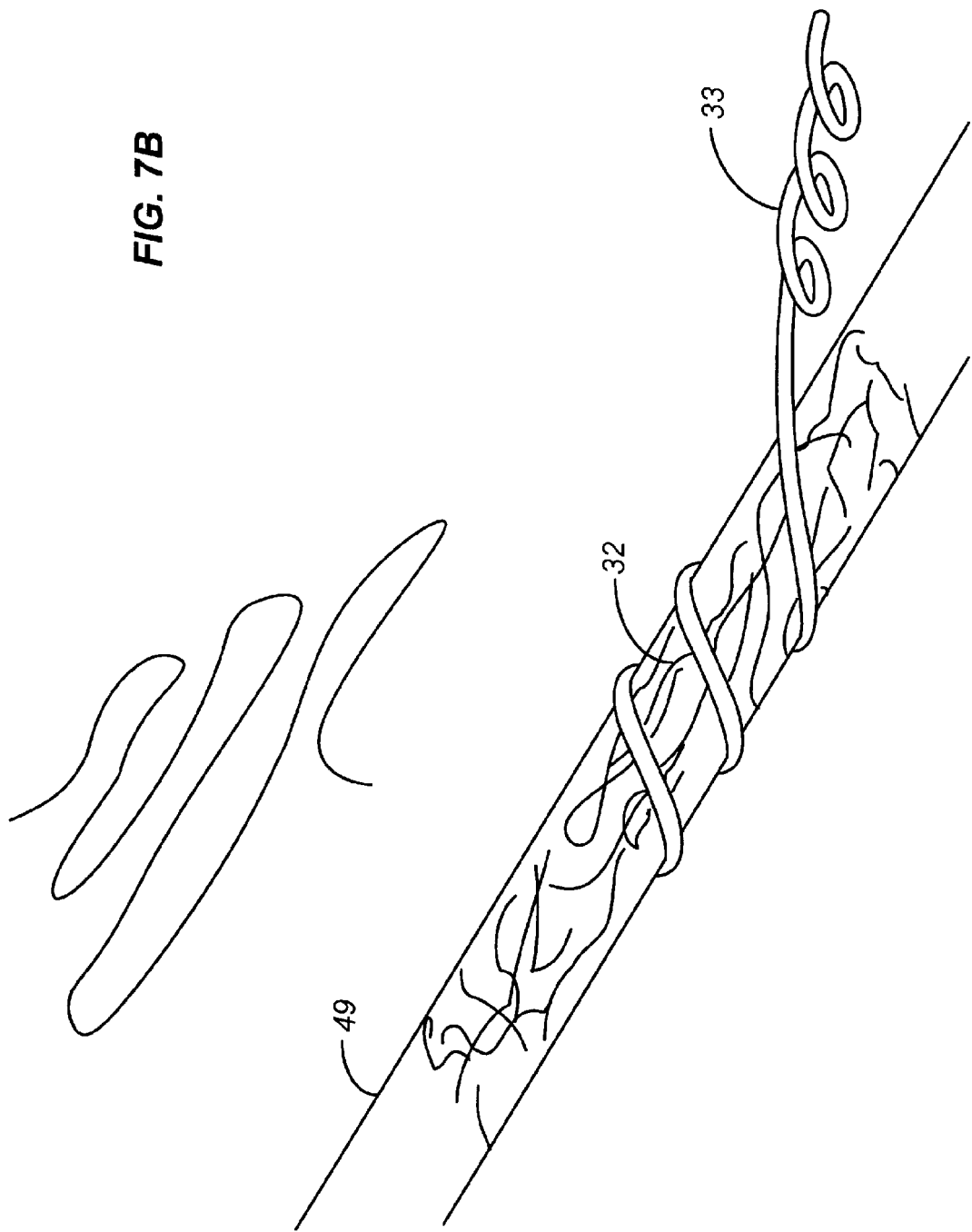
FIG. 7B is an enlarged view of a portion of the electrospinning apparatus of FIG. 5, illustrating the deposition of a randomly aligned fiber layer on the mandrel.
Figure 8:
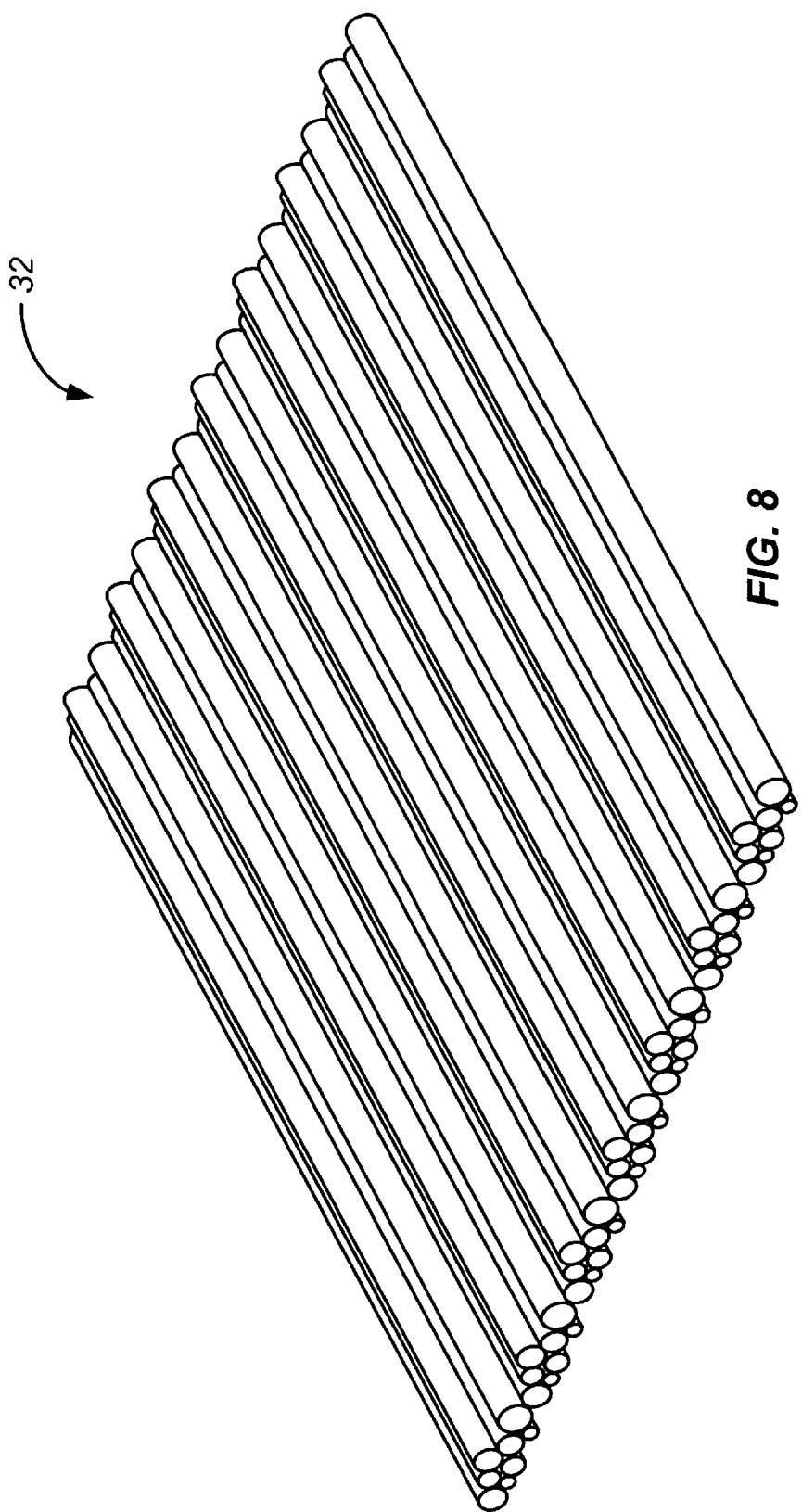
FIG. 8 is an illustration of a longitudinally aligned polymer sheet for forming the body of FIG. 1A.
Figure 9:
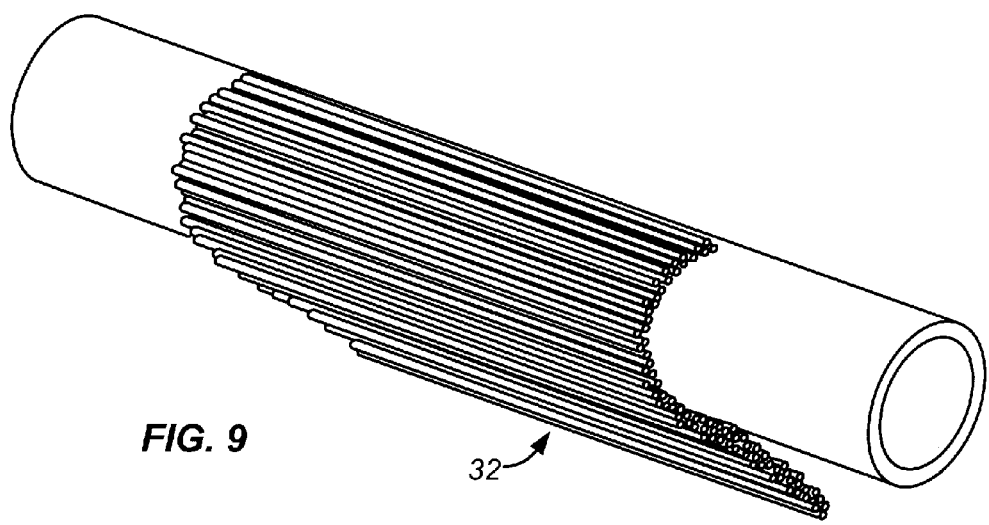
FIG. 9 is a schematic diagram showing the rolling process for creating the tubular body of FIG. 1A with the sheet of FIG. 8. The sheet is rolled around a rod and later sutured, fastened, or adhered along the seam.

In an exemplary embodiment, the mandrel and spinnerets are separated by approximately 22 cm. Referring to FIGS. 6, 7A, and 7B, the spinnerets reciprocate along a longitudinal axis of the spinning mandrel to create a layer of polymer fibers. In various embodiments, the rotation speed and movement of the spinnerets are controlled to create a layer of polymer fibers having a substantially uniform thickness. In various embodiments, the thickness is about 0.7 mm. In various embodiments, the thickness is between about 0.5 mm and about 1.0 mm.

In one aspect, the fibrous polymer body and/or outer layer includes electrospun fibers aligned in an orientation desired by the user. In an exemplary embodiment, the layers are aligned in an essentially longitudinal or essentially circumferential direction. The fibrous polymer body and/or outer layer can either have a seam or they can be seamless. In another exemplary embodiment, the fibrous polymer body and/or outer layer are seamless along an axis essentially parallel to the longitudinal axis of the polymer body.

In one embodiment, the fibrous polymers of use in the invention can be created on a mandrel with at least two conducting regions and at least one non-conducting region. Such a mandrel can be designed in a number of ways. An exemplary depiction of a mandrel as part of an apparatus for producing sheets and/or conduits of the invention is described in FIGS. 4, 5, 6, and 7A. In one instance, a region of a conducting mandrel can be covered with a non-electrically conducting material. In an exemplary embodiment, the non-electrically conducting material is a member selected from tape, electrical tape, teflon and plastic to enable removal of the device.

Although described in terms of electrospinning, various components of the device may be produced by other methods including, but not limited to, cutting or etching a design from a tubular stock or flat sheet, rolling more interwoven wires or braids, and the like.

After the body 32 is formed, the body is wrapped with support structure 33 in Step S2. Exemplary support 33 is an extruded filament which is spirally wound around the body (FIG. 7B). The filament is wound around the body with sufficient tightness to fit snugly around the body.

In an exemplary embodiment, the support structure is a polymer filament. The support structure may be added during the electrospinning process. The support structure may be wound manually or using conventional machinery.

Filament 33 may be formed by manually wrapping polymer material around a spirally cut mandrel of similar diameter to mandrel 49 used to form fibrous body 32. The filament may also be wrapped directly onto the electrospun body. The filament is heated and allowed to cool on an outer surface of the body.

In Step S3, a poly(urethane) outer layer is electrospun around the filament and body as an overwrap layer to form the intermediate, uncoated graft device. Outer layer 37 is provided around at least a portion of the support structure. The outer layer may be formed separately or formed directly over the support structure and body.

The outer layer may be formed by an electrospinning process similar to the process used to form body 32. In various embodiments, the outer layer is formed by electrospinning polymer fibers using the same system by directly spinning the fibers over support structure 33 and/or body 32 while they are still on mandrel 49. In various embodiments, some or all of the above steps are performed while the preceding material is partially wet.

The fibers of the exemplary outer layer intimately contact the outer surface of the device. The contact between the outer layer fibers and the filament and/or body results in the outer layer adhering to the surface of the device. In various embodiments, the outer layer is electrospun over the filament when the device is still partially wet. In various embodiments, the outer layer is formed separately and thereafter assembled over the filament-wrapped body. The exemplary assembled device including the body, filament, and outer layer is referred to in various aspects as the "uncoated device".

Figure 3:
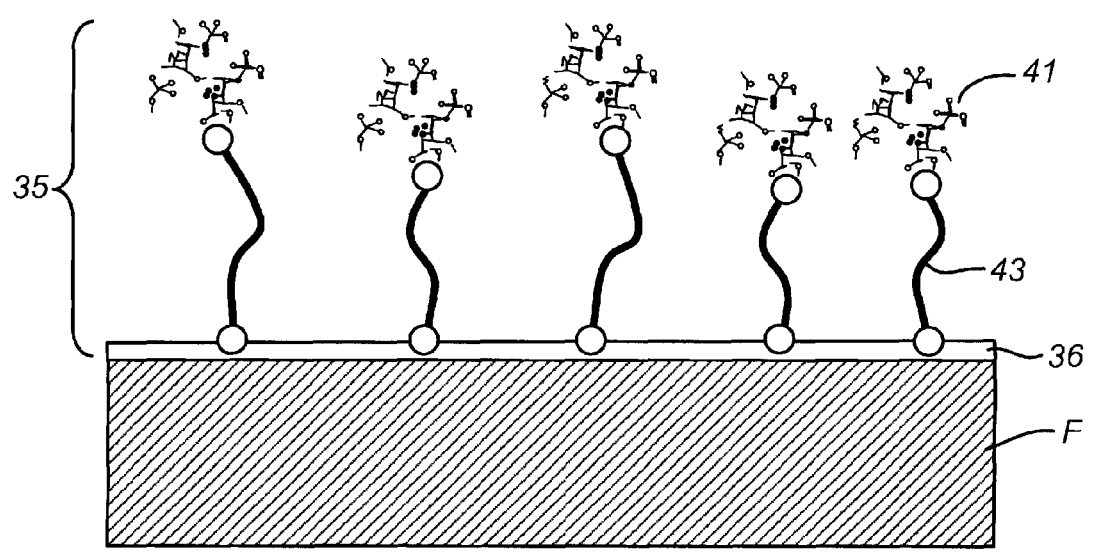
FIG. 3 is a schematic view of a portion of an electrospun fiber of the body or outer layer, illustrating a plurality of bioactive agents attached to the fiber.

Referring to FIGS. 3 and 11, covering composition 35 is applied to the uncoated device. The uncoated device is first treated with polymer primer 36 in Step S4 and then functionalized with a heparin residue in Steps S5 and S6. The exemplary covering composition includes poly(lactide) (PLA) attached to a heparin residue through a linker molecule. In various embodiments, the outer layer is allowed to completely dry before coating the device with the polymer primer. In various embodiments, the outer layer is allowed to partially dry before coating the device with the polymer primer. The method for attaching the polymer primer will be described in more detail below.

In various embodiments, Steps S4, S5, and S6 are accomplished by successive dip coating of the device. FIG. 3 illustrates an exemplary fiber "F" of the fibrous body which is covered with polymer primer 36 in accordance with the present invention. In general, the dip coating operations are performed with a reagent under sufficient conditions to achieve sufficient attachment for the particular clinical application. Further details regarding the exemplary dip coating operations are provided below and in the Examples.

In Step S4, the exemplary device is dip coated in a polymer primer solution including poly(lactide) (PLA) in acetonitrile. The device is dipped in the PLA coating under sufficient conditions to cause attachment to a respective fiber or fibers "F". The dipped device is then dried at low temperature, relatively low humidity and normal atmospheric pressure until the acetonitrile has evaporated.

The exemplary device is dipped in the polymer primer solution under sufficient conditions to cause the polymer primer to attach to the device thereby forming a layer of polymer primer on the fibers (see, e.g., FIG. 3). In various embodiments, the polymer primer layer is attached to the device by adsorption. In the exemplary embodiment, the polymer primer layer is integrated into the device and coats one or more of the fiber components of the device. The polymer primer may coat the fibers in the body, outer layer, or both. The polymer primer may also coat the support filament. In various embodiments, essentially all the fibers in the body are coated with the polymer primer. In various embodiments, essentially all the fibers in the outer layer are coated with the polymer primer. In various embodiments, some of the fibers in the body are coated with the polymer primer. In various embodiments, some of the fibers in the outer layer are coated with the polymer primer.

In Step S5, the exemplary coated device is dip coated in a linker molecule solution including poly(ethylene glycol) ("PEG"). The device is placed in the solution under sufficient conditions to cause the PEG to be immobilized to the device. In various embodiments, the PEG is immobilized to the surface of the polymer primer. The PEG can be immobilized by treating it with EDC (i.e., 1-ethyl-3(3-dimethylaminopropylcarbodiimide) to facilitate covalent bonding with the carboxyl group of the exemplary polymer primer.

The device is dipped in the solution including PEG and a reagent under sufficient conditions to cause the PEG to attach to the polymer primer. In various embodiments, the reagent is forced to evaporate from the device after the dipping. In an exemplary embodiment, EDC is added to the solution of PEG shortly before treating the device. In the exemplary embodiment, the PEG is integrated into the device. The PEG may attach to the polymer primer covering the fibers in the body, outer layer, or both. The PEG may also attach to the polymer primer covering the support filament. In various embodiments, PEG is attached to essentially all of the free ends of the poly(lactide) forming the polymer primer. In various embodiments, PEG is attached to only a portion of the free ends.

In Step S6, the device is dip coated in a solution of heparin sodium. In an exemplary embodiment, EDC is added to the solution of heparin sodium shortly before treating the device. In various embodiments, the heparin sodium is covalently attached to the PEG. In an exemplary case, the PLA primer is attached to a surface of a fiber of body 32, one end of the PEG linker is attached to an end of a respective PLA molecule, and an opposite end of the PEG linker is attached to an end of the respective heparin residue.

One will appreciate that the level and amount of attachment of the polymer primer and/or covering composition to the respective fibrous component, the linkers to the polymer primer, and the bioactive agent to the linkers may vary depending on the application. In various embodiments, essentially all of the fibers are coated with polymer primer. "Essentially all" refers to substantially or most of the fibers and may include, for example, 100%, 95%, 90%, 80%, 70%, and 60%.

In various embodiments, the linkers are attached to about 100% of the polymer primer. In various embodiments, the linkers are attached to about 95% of the polymer primer. In various embodiments, the linkers are attached to about 90% of the polymer primer. Attachment of the linkers refers to attachment of a linker molecule to a unit of the polymer primer such as a poly(lactide) molecule. In various embodiments, linkers are attached to essentially all of the polymer primer.

In various embodiments, essentially 100% of each of the linkers is attached to a bioactive agent. In various embodiments, essentially 95% of each of the linkers is attached to a bioactive agent. In various embodiments, essentially 90% of each of the linkers is attached to a bioactive agent. In various embodiments, essentially all of the linkers are attached to a bioactive agent.

In various embodiments, the linker molecule is PEG, and the PEG is immobilized to the surface of the poly(lactide) primer layer using carbodiimide chemistry (i.e., activation of free carboxylic acid residues of the PLA polymer primer with 1-ethyl-3-[3-dimethylaminopropyl]carbodiimide ("EDC") and subsequent reaction with one of the functional ends of di-amino PEG). In various embodiments, the heparin residue is attached to the linker molecule using carbodiimide chemistry (i.e., activation of free carboxylic acid residues on the heparin with EDC and subsequent reaction with the remaining functional end of the immobilized linker molecule). In various embodiments, the linker molecule tethers the heparin from the surface of the respective polymer fiber (best seen in FIG. 3).

After addition of the bioactive agent, the device is washed with Phosphate Buffered Saline and Molecular Biology Grade Water to remove any excess heparin. The device may also be optionally washed after applying the polymer primer, the linker molecule layer, or both.

The exemplary coated device has an intraluminal and an extraluminal surface coated by the polymer primer. In various embodiments, the covering composition is integrated into the device and fills interstices between the fibers of the device. The device includes a first longitudinal terminus and a second longitudinal terminus.

The process for making the device in accordance with the invention may include further processing operations between any of the above steps or post-processing. For example, the device may be cut and laid out into a flat sheet. The finished device is dried, packaged and sterilized.

The device of the invention can be formed into a variety of shapes, depending on the nature of the problem to be solved.

In various embodiments, the device is an artificial blood vessel. The artificial blood vessel may be in various configurations including, but not limited to, a straight or bent tube, a loop, an anastomosis, or a bifurcate.

In an exemplary embodiment, the device has the shape of a sheet or membrane. The sheet may be produced by forming a tubular shape as described above and then cutting the device along a longitudinal line and laying it out in a sheet shape. With particular reference to FIG. 10, in an exemplary embodiment, the device is formed as a 'criss-cross' sheet. To form a criss-cross sheet, layers of aligned sheets are formed as described above and arranged in relation to each other.

In various embodiments, the device has the shape of a conduit. A conduit can have a variety of sizes, depending on its length, as well as its inner diameter and outer diameters. These parameters can be varied to accommodate, for example, various tissue sizes and applications. In an exemplary embodiment, the device is rolled to fabricate a conduit with a seam.

Some applications may call for fastening one end of the device to itself, for example, to form a conduit with a seam. The fastening can be accomplished by annealing (heat), adhesion or by sutures. Examples of adhesion involve solvents or biological adhesives such as fibrin sealant and collagen gels.

In various embodiments, the device is configured as an expandable stent. To form a stent, the device is formed as described above and attached to a stent scaffold. In various embodiments, a stent system is provided for repairing a region of vascular injury involving a bifurcation of the vasculature. For example, the device may be configured for repairing an aneurysm in an abdominal aorta.

Other stent architectures will be apparent to those of skill in the art from the description herein. For example, the devices of the invention can also include a valve, e.g., a one way valve, for inlet and output of blood, emboli, gas, and air. The lengths of the exemplary device may also vary from about 1 mm to about 30 mm depending on the application. For example, a peripheral vascular stent/stent graft is optionally from about 6 mm to about 15 mm in diameter. A wall stent (carotid or arterial) is from about 5 mm to 10 mm in diameter. An exemplary bronchial/lung segment stent of the invention is from about 5 mm to about 20 mm in length. An exemplary coronary artery stent is from about 2 to about 4 mm in diameter.

Attachment of Bioactive Agent

In various embodiments, the bioactive agent is covalently bonded to a reactive group located on one or more components of the polymer primer or fibers of the device directly or through a linker molecule. Approaches for attaching the bioactive agent include the use of coupling agents that serve as attachment vehicles for coupling reactive groups of biologically active molecules to reactive groups on a monomer or a polymer.

Complementary reactive functional groups and classes of reactions useful in practicing the present invention are generally those in the art of bioconjugate chemistry. In various embodiments, the classes of reactions available with reactive functional groups of the invention are those which proceed under relatively mild conditions.

Useful reactive functional groups include, for example:
(a) carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters; and (b) amine groups, which can be, for example, acylated, alkylated or oxidized.

The reactive functional groups can be chosen such that they do not participate in, or interfere with, the reactions necessary to assemble the compound of the invention. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In an exemplary embodiment, a carboxylic acid moiety is being attached to an amine moiety. First the carboxylic acid moiety is reacted with a carbodiimide to generate an O-acylisourea, which can react with the amine moiety to produce an amide which then links the two moieties.

In an exemplary embodiment, attachment of bioactive agents to the fibrous body and/or outer layer described herein can be achieved by any of several methods. For example, a bioactive agent can be attached by treatment with EDC (i.e., 1-ethyl-3(3-dimethylaminopropylcarbodiimide), which will facilitate linkage of, for example, the amino end of linker 43 to the carboxyl group of the PLA primer layer 36 or bioactive agent 41. The linkages may be on the opposite species as well (e.g. the amino group could be on an end of the fibrous polymer). One will appreciate from the description herein that other coupling agents may be used.

Reactive groups contemplated in the practice of the present invention include functional groups, such as carboxyl, carboxylic acid, amine groups, and the like, that promote physical and/or chemical interaction with the bioactive material. The particular compound employed as the modifier will depend on the chemical functionality of the biologically active agent and can readily be deduced by one of skill in the art. In the present embodiment, the reactive site binds a bioactive agent by covalent means. It will, however, be apparent to those of skill in the art that these reactive groups can also be used to adhere bioactive agents to the polymer by hydrophobic/hydrophilic, ionic and other non-covalent mechanisms.

Bioabsorbable, Biodegradable, and Bioresorbable Fiber Materials

Polymer compositions, such as body 32, outer layer 37, support structure 33, and covering composition 35 may have intrinsic and controllable biodegradability, so that they persist for about a week to about six months. The fibers may also be biocompatible, non-toxic, contain no significantly toxic monomers and degrade into non-toxic components. In various embodiments, one or more of the polymer compositions is chemically compatible with the substances to be delivered and tends not to denature the active substance. In various embodiments, one or more of the polymer compositions becomes sufficiently porous to allow the incorporation of biologically active molecules and their subsequent liberation from the fiber by diffusion, erosion or a combination thereof. The polymer compositions may remain at the site of application by adherence or by geometric factors, such as by being formed in place or softened and subsequently molded or formed into fabrics, wraps, gauzes, particles (e.g., microparticles), and the like.

Methods of Treatment with the Device

In various exemplary embodiments, the invention provides a method of supporting and/or repairing blood vessels by implanting device 30 in the subject vessel. In another aspect, a method of treating a vascular disease such as atherosclerosis and stenosis is provided. This method involves contacting the vascular disease site with the device of the invention. Exemplary vascular diseases treatable by this method include atherosclerosis, stenosis and a combination thereof.

In an exemplary embodiment, a method of treating an injury comprising a severed anatomical structure of essentially tubular cross-section is provided. An exemplary severed anatomical structure comprises a first severed stump and a second severed stump. The method includes interposing the device of the invention between the first severed stump and the second severed stump such that both the first longitudinal terminus and the second longitudinal terminus of the device contact a member selected from the first severed stump, a region of the anatomical structure distal to the first severed stump and combinations thereof and a member selected from the second severed stump, a region of said anatomical structure distal to the second severed stump and combinations thereof, respectively. On proper orientation of the device, the first longitudinal terminus is fastened to the member selected from the first severed stump, the region of the anatomical structure distal to the first severed stump and combinations thereof, and the second longitudinal terminus to the member selected from the second severed stump, a region of the anatomical structure distal to the second severed stump and combinations thereof, forming a patent anatomical structure, thereby treating the injury.

As will be appreciated by those of skill, the device of the invention is deployable by conventional methods, including but not limited to, catheters, partial or full vascular cutdowns and the like. In an exemplary embodiment, the device is deployed by a guide wire or through a catheter to the appropriate/desired location in the body.

The invention is further illustrated by the Examples that follow. The Examples are not intended to define or limit the scope of the invention.

EXAMPLES

Example 1

Preparation of Fiber Graft Functionalized with Heparin

Poly(urethane) (PU) (DSM Polymer Technology Group of Berkeley, Calif.) was used to fabricate the fibrous polymer body by electrospinning. The PU was dissolved in N,N-dimethylformamide (DMF) to approximately 22% weight/volume. The PU solution was delivered by a programmable pump through the exit hole of an electrode (spinneret) to a stainless steel mandrel surface.

The poly(urethane) material was electrospun in a controlled environment of about 40 degrees Celsius and about 15-20% local, relative humidity. The temperature was controlled using infrared (IR) heat. The height of the spinnerets above the mandrel was fixed at approximately 22 cm from the mandrel. The electrospun fibers were allowed to dry between the exit hole of the spinnerets and the mandrel surface.

The spinnerets moved along a longitudinal axis of the mandrel during the spinning process to create a uniformly thick layer of randomly aligned fibers. The PU was applied to the surface to a thickness of approximately 0.7 mm.

A filament was provided as a support structure on the device. The filament was fabricated from poly(ether urethane) (PEU) (DSM Polymer Technology Group). The PEU was melted and extruded to a filament having a diameter of about 0.028 inches. The filament was subsequently manually wrapped around a spirally cut mandrel of similar diameter as the mandrel used during the construction of the first layer—the fibrous body. The filament was then heated to approximately 100 degrees Celsius for 45 minutes to thermo-set the filament into the spiral configuration. The filament was allowed to cool at room temperature for a minimum of one hour. This filament was then placed onto the exterior wall of the electrospun body. The pitch of the spirally-wound filament was 3.969 mm, which was determined to be sufficient to prevent kinking with a bend radius well below 19 mm.

The spiral filament was fastened to the inner body wall by electrospinning an outer layer around the entire filament and body structure. The outer layer was fabricated from poly (urethane) (DSM Polymer Technology Group of Berkeley, Calif.) similar to that used for the body.

The process and environment for forming the outer layer was the same as that for electrospinning the body. The temperature of the electrospinning environment was lowered slightly, and the fibers were allowed to remain slightly wet when they contacted the filament and body on the mandrel. The outer layer was applied to a thickness of 0.1 mm.

The assembled device was then treated with a polymer primer and bioactive agent. The device was first dipped in a coating solution of 1% w/v poly(lactide) (PLA) (PURAC America of Lincolnshire, Ill., 2.0 dL/g inherent viscosity midpoint) in a solvent. Following the above-described process, each individual fiber of the respective layers was coated or encapsulated by a layer of PLA primer. The solvent was then left in normal atmospheric pressure at below room temperature until the solvent evaporated from the device.

The device was then dipped in a solution including a linker molecule to cause the linker molecules to become immobilized to the surface of the PLA primer using carbodiimide chemistry (e.g., activation of free carboxylic acid residues of the PDLA covering with 1-ethyl-3-[3-dimethylaminopropyl] carbodiimide ("EDC") and subsequent reaction with one of the functional ends of polyoxyethylene bis(amine)). The linker molecule solution included polyoxyethylene bis (amine) (poly(ethylene glycol) (PEG)) (Sigma Aldrich (P/N P9906)). EDC was added to the linker molecule solution in a 0.1M 2-(N-morpholino)ethanesulfonic ("MES") acid buffer shortly before treatment of the device. The PEG was of a linear structure and had an average molecular weight of 3350 g/mol. The average molecular weight of the PEG may be between about 1000 and 10,000 g/mol. The PEG was reacted to the dried device for at least about two hours at room temperature and then washed.

Thereafter, the device including the PLA primer and PEG attached to the fibers was dipped in a third solution including heparin for several hours. Reagents were put into the heparin solution shortly before treatment of the device. The heparin was attached to the polyoxyethylene bis(amine) using carbodiimide chemistry (e.g., activation of free carboxylic acid residues on the heparin with EDC and subsequent reaction with the remaining functional end of the immobilized amino PEG).

The solution included Heparin Sodium (Scientific Protein Laboratories, LLC of Waunakee, Wis., 182 U/mg). EDC was added to the solution with pH 7.4 phosphate buffered saline ("PBS") shortly before treatment. The linker (PEG) was found to tether the heparin from the surface of the respective polymer fiber. The coated product was left in the heparin solution at room temperature long enough to allow the heparin to react with the PEG.

The assembled graft device was then washed with Phosphate Buffered Saline and Molecular Biology Grade Water at room temperature to remove any excess heparin. The graft was then dried, packaged and sterilized.

Figure 2A:
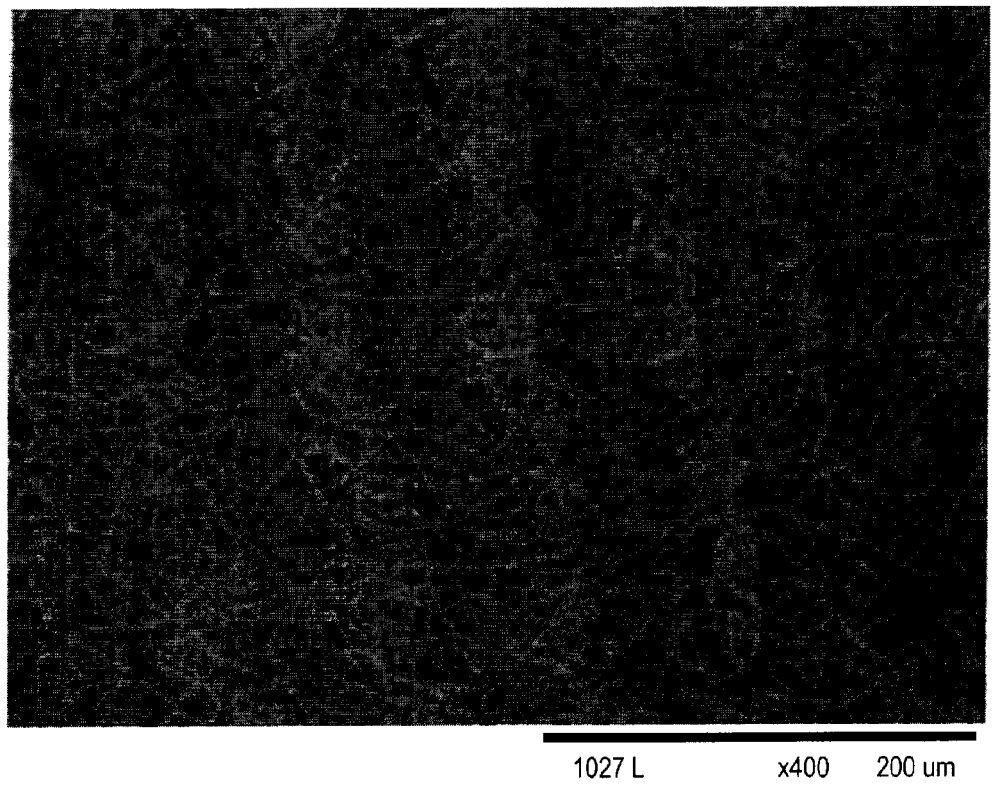
FIG. 2A is a scanning electron microscope (SEM) image of the lumen of the device body of FIG. 1A. The body includes a plurality of electrospun, randomly-aligned polymer fibers.
Figure 2B:
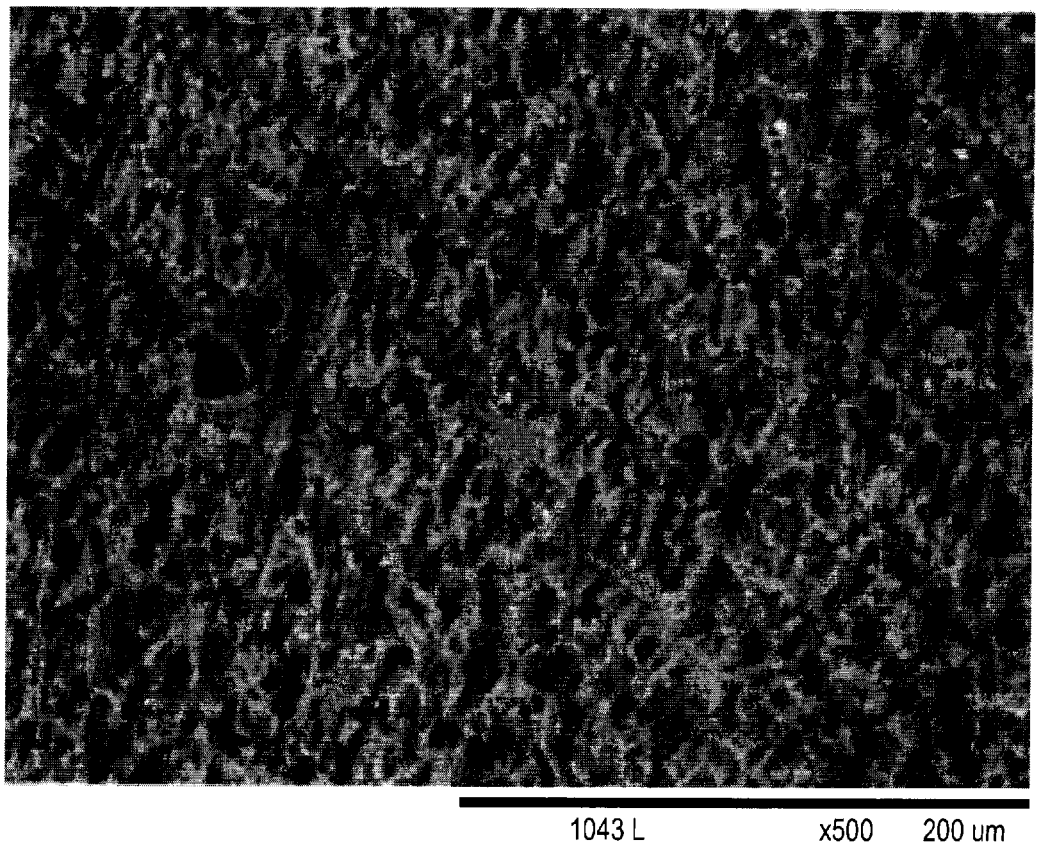
FIG. 2B is a SEM image of a cross-section of the wall body of FIG. 2A.
Figure 12:
FIG. 12 is a front view of the device of FIG. 1A bent at a nearly zero radius.

The assembled device was a vascular graft which was about 30 cm in length. Scanning electron microscopy (SEM) was used to visualize the assembled device. A SEM image of the lumen is shown in FIG. 2A, and a SEM image of the outer layer is shown in FIG. 2B. The SEM images show that the electrospinning resulted in random alignment of the fibers. The device was found to meet clinical standards for burst strength, dynamic compliance, porosity, longitudinal tensile strength, suture retention strength, water entry pressure, and kink resistance. FIG. 12 illustrates the device bent at a nearly zero diameter and well less than 19 mm.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An implantable medical device comprising:
a fibrous polymer body comprising electrospun poly(urethane) fiber;
a support filament wrapped around the body;
an outer layer around the filament for adhering the filament to the body, the outer layer comprising electrospun poly (urethane) fiber; and
a covering composition covering the fiber of the body, the covering composition comprising poly(lactide) and having the formula:

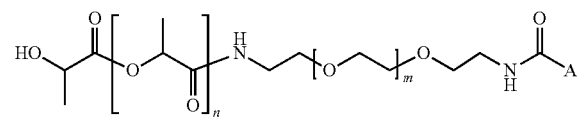

wherein A is a heparin residue, n is an integer between about 1000 and about 10000, and m is an integer between about 50 and about 100.

2. The device according to claim 1, wherein the body comprises a plurality of thermoplastic poly(urethane) fibers.

3. The device according to claim 1, wherein the filament comprises thermoplastic polyether urethane.

4. The device according to claim 3, wherein the filament is configured to prevent kinking of the device when bending at a radius greater than about 1 mm.

5. The device according to claim 4, wherein the filament is spirally wound around the body and has a pitch of between about 1 mm and about 6 mm.

6. The device according to claim 5, wherein the filament is spirally wound around the body and has a pitch of about 4 mm.

7. The device according to claim 1, wherein the filament is configured to provide a degree of anti-kinking resistance to the device.

8. The device according to claim 1, wherein the outer layer comprises a plurality of thermoplastic poly(urethane) fibers.

9. The device according to claim 1, the body and outer layer each comprising a plurality of electrospun fibers, wherein essentially all of the fibers of the body and outer layer are covered with the covering composition.

10. The device according to claim 1, wherein the body is monolithically formed and the covering composition is integrated into the body by dip coating.

11. The device according to claim 1, the body comprising a plurality of electrospun fibers, wherein the covering composition layer fills interstices between the plurality of fibers.

12. The device according to claim 1, wherein the covering composition is attached to the body by adsorption.

13. The device according to claim 1, wherein A is heparin sodium.

14. The device according to claim 1, wherein the device is a tubular vascular graft.

15. The device according to claim 1 produced by the process comprising:
- electrospinning the fibrous polymer body, the body comprising a plurality of electrospun fibers;
- wrapping the support filament around the electrospun body;
- providing the electrospun outer layer around the filament to adhere the filament to the body thereby forming an uncoated device;
- applying a polymer primer comprising poly(lactide) in a solution to the uncoated device under sufficient conditions to cause attachment of the polymer primer to at least one of the plurality of fibers of the body;
- after the applying, immobilizing a linker molecule to the applied polymer primer, the linker molecule forming a covalent bond with the primer; and
- after the immobilizing, covalently attaching the heparin residue to the immobilized linker molecule thereby forming the covering composition on the at least one fiber.

16. The device according to claim 15, wherein the polymer primer has an inherent viscosity midpoint of about 2.0 dl/g at room temperature.

17. The device according to claim 16, wherein the applying is performed under sufficient conditions such that essentially all of the plurality of fibers of the body are covered with the polymer primer.

18. The device according to claim 16, wherein the applying, immobilizing and attaching are accomplished by successive dip coating.

* * * * *